(12) United States Patent
Oluwasakin et al.

(10) Patent No.: US 12,740,875 B2
(45) Date of Patent: Sep. 22, 2026

(54) LEG LENGTH AND OFFSET TRACKING WITH EXPANDABLE TRIAL FEMORAL ASSEMBLY

(71) Applicant: GLOBUS MEDICAL, INC., Audubon, PA (US)

(72) Inventors: Israel Oluwasakin, Dresher, PA (US); Edward McGettigan, Norristown, PA (US); Hayden Cameron, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 87 days.

(21) Appl. No.: 18/801,924

(22) Filed: Aug. 13, 2024

(65) Prior Publication Data

US 2026/0047941 A1 Feb. 19, 2026

(51) Int. Cl.
*A61F 2/46* (2006.01)

(52) U.S. Cl.
CPC .... *A61F 2/4657* (2013.01); *A61F 2002/4658* (2013.01)

(58) Field of Classification Search
CPC .................. A61F 2/4657; A61F 2/3601; A61F 2002/4658; A61F 2250/0048
See application file for complete search history.

(56) References Cited

U.S. PATENT DOCUMENTS 4,150,293 A 4/1979 Franke
5,246,010 A 9/1993 Gazzara et al.
5,354,314 A 10/1994 Hardy et al.
5,397,323 A 3/1995 Taylor et al.
5,598,453 A 1/1997 Baba et al.
5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
(Continued)

OTHER PUBLICATIONS

US 8,231,638 B2, 07/2012, Swarup et al. (withdrawn)

*Primary Examiner* — Andrew Yang

(57) ABSTRACT

Methods include tracking one or more of a leg length or an offset in a patient during a total hip arthroplasty (THA) procedure performed using a navigated surgical system, with an expandable trial femoral assembly. Certain methods include registering a pelvis of the patient to the navigated surgical system; and in various embodiments measuring a leg length or registering a femur to the navigated surgical system. An expandable trial femoral assembly is affixed to a prepared and broached femur of the patient; and the expandable trial femoral assembly is reduced into an acetabular prosthesis. A navigated driver may then be used to adjust an expansion extent of the expandable trial femoral assembly. The navigated surgical system may measure the leg length and the offset in the patient based on the movement of a reference element of the femur relative to a reference element of the pelvis.

7 Claims, 26 Drawing Sheets

(56) References Cited

U.S. PATENT DOCUMENTS 6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,425,214 B1 * 9/2008 McCarthy ............. A61F 2/4684 606/89
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan
7,834,484 B2 11/2010 Sartor

(56) References Cited

U.S. PATENT DOCUMENTS 7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Willliams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Issacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.

(56) References Cited

U.S. PATENT DOCUMENTS 8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.
8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,247,998 B2 * 2/2016 Hladio .................. A61B 90/70
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 12/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 von Jako
2008/0109012 A1 5/2008 Falco et al.

(56) References Cited

U.S. PATENT DOCUMENTS

2008/0144906 A1 6/2008 Allred et al.
2008/0161680 A1 7/2008 von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Gratacos Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0221819 A1 8/2014 Sarment
2014/0222023 A1 8/2014 Kim et al.

(56) References Cited

U.S. PATENT DOCUMENTS

2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.
2014/0303434 A1 10/2014 Farritor et al.
2014/0303643 A1 10/2014 Ha et al.
2014/0305995 A1 10/2014 Shelton, IV et al.
2014/0309659 A1 10/2014 Roh et al.
2014/0316436 A1 10/2014 Bar et al.
2014/0323803 A1 10/2014 Hoffman et al.
2014/0324070 A1 10/2014 Min et al.
2014/0330288 A1 11/2014 Date et al.
2014/0364720 A1 12/2014 Darrow et al.
2014/0371577 A1 12/2014 Maillet et al.
2015/0039034 A1 2/2015 Frankel et al.
2015/0085970 A1 3/2015 Bouhnik et al.
2015/0146847 A1 5/2015 Liu
2015/0150524 A1 6/2015 Yorkston et al.
2015/0196261 A1 7/2015 Funk
2015/0213633 A1 7/2015 Chang et al.
2015/0335480 A1 11/2015 Alvarez et al.
2015/0342647 A1 12/2015 Frankel et al.
2016/0005194 A1 1/2016 Schretter et al.
2016/0166329 A1 6/2016 Langan et al.
2016/0235480 A1 8/2016 Scholl et al.
2016/0249990 A1 9/2016 Glozman et al.
2016/0302871 A1 10/2016 Gregerson et al.
2016/0320322 A1 11/2016 Suzuki
2016/0331335 A1 11/2016 Gregerson et al.
2017/0135770 A1 5/2017 Scholl et al.
2017/0143284 A1 5/2017 Sehnert et al.
2017/0143426 A1 5/2017 Isaacs et al.
2017/0156816 A1 6/2017 Ibrahim
2017/0202629 A1 7/2017 Maillet et al.
2017/0212723 A1 7/2017 Atarot et al.
2017/0215825 A1 8/2017 Johnson et al.
2017/0215826 A1 8/2017 Johnson et al.
2017/0215827 A1 8/2017 Johnson et al.
2017/0231710 A1 8/2017 Scholl et al.
2017/0258426 A1 9/2017 Risher-Kelly et al.
2017/0273748 A1 9/2017 Hourtash et al.
2017/0296277 A1 10/2017 Hourtash et al.
2017/0360493 A1 12/2017 Zucher et al.

* cited by examiner

FIG. 4

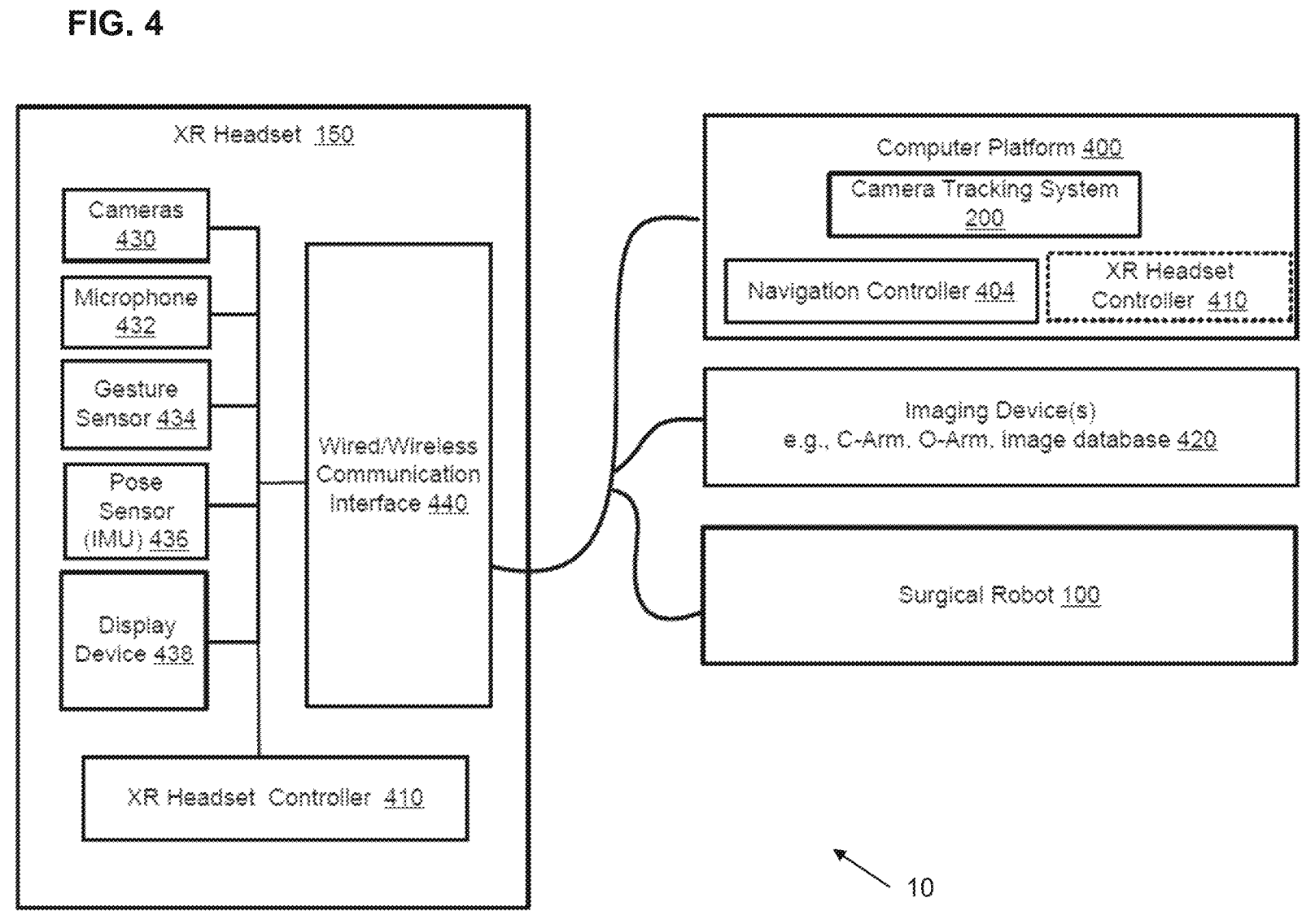

Computer Platform 400

Camera Tracking System 200

XR Headset Controller 410

Navigation Controller 404

Imaging Device(s) e.g., C-Arm, O-Arm, image database 420

Surgical Robot 100

10

XR Headset 150

Wired/Wireless Communication Interface 440

Cameras 430

Microphone 432

Gesture Sensor 434

Pose Sensor (IMU) 436

Display Device 438

XR Headset Controller 410

FIG. 5

Position Patient on OR Table
500

Register Patient
600

Intraoperative Computer Navigated Surgery
700

1100
1102
Register Pelvis
1104
Measure Native Leg Length with Stylus
1106
Prepare Acetabulum and Place Trials/Implants
1108
Prepare Femur and Broach
1110
Reduce Joint with expanding neck trial
1112
Measure leg length and offset with navigated expansion tool and moving marker

Figure 25:
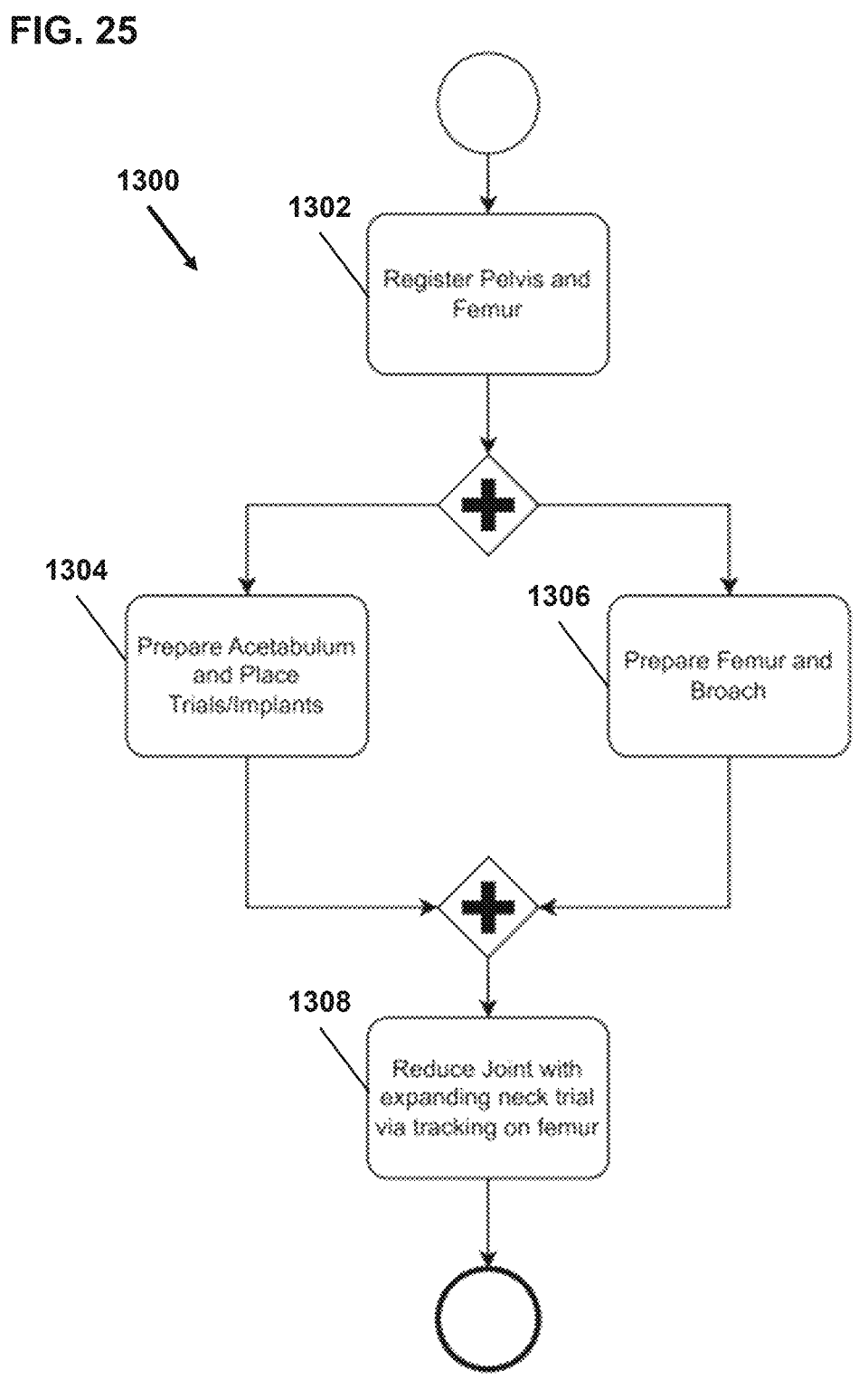

Register Pelvis and Femur

1304

Prepare Acetabulum and Place Trials/Implants

1306

Prepare Femur and Broach

1308

Reduce Joint with expanding neck trial via tracking on femur

LEG LENGTH AND OFFSET TRACKING WITH EXPANDABLE TRIAL FEMORAL ASSEMBLY

BACKGROUND OF THE INVENTION

The disclosure relates generally to devices, systems, and methods for use in navigated total hip arthroplasty (THA) procedures. More particularly, the invention relates to methods and systems for tracking one or both of a patient's leg length or offset during a THA procedure using a navigated surgical system and an expandable trial femoral assembly.

Total hip arthroplasty, or hip replacement, is a surgical procedure used to resurface and reconstruct a hip joint that has been damaged by disease or injury, e.g., by arthritis or a fracture. THA devices replace both the acetabulum and the femoral head that collectively comprise the hip joint.

The replacement process includes preparation of the acetabulum, e.g., by reaming, and preparation of the femoral canal including, e.g., broaching and/or reaming. The surgeon may then place one or more trial components and reduce the joint to find the right range of motion, soft tissue balance, and leg length for the patient. The trial components include a trial acetabular prosthesis, and trial femoral heads and trial femoral necks. A surgeon may trial multiple different offset options to find the best fit for the patient. Trial heads are typically offered in sizes 28 millimeters (mm), 32 mm, and 36 mm. The 28-mm heads may be offered in offsets of −5 mm, −3.5 mm, 0 mm, +3.5 mm, +7 mm, +10.5 mm, and +12 mm. The 32 mm and 36 mm trial heads may be offered in −3.5 mm, 0 mm, +3.5 mm, +7 mm, and +10.5 mm. Trial necks may be offered in standard and lateralized options in three sizes, for use with stems 1/2/3/4, 5/6/7/8, and 9/10/11/12, for each size for a total of six trial necks. In addition to the foregoing options, expandable trial femoral assemblies having adjustable necks are described in U.S. patent application Ser. No. 18/454,47, filed on Aug. 23, 2023, which is hereby incorporated by reference as though fully set forth herein. The use of an expandable trial femoral assembly allows a surgeon to identify an appropriate trial implant without dislocating the patient's joint. The use of expandable trial femoral assemblies also reduces the number of stock keeping units (SKUs) for trial heads and trial necks required on instrument trays during THA procedures and maintained in stock at the hospital or surgical center.

Following trialing, the THA procedure is completed by securing an acetabular prosthesis to the prepared acetabulum, thereby forming a replacement articulating surface which interfaces with a femoral head and neck secured to the end of the femur. The femoral implant is pivotably coupled to the acetabular implant, thereby reconstructing the hip joint. Exemplary acetabular implants are disclosed in, e.g., U.S. patent application Ser. No. 17/024,876, filed Sep. 18, 2020 (published as US 2022/0087823 A1), which is incorporated by reference as though fully set forth herein.

When using expandable trial femoral assemblies, it is desirable to track the leg length and offset produced by a particular trial implant and expansion extent thereof in real time or approximate real time. It is also desirable to enable collection, analysis, and display of leg length and offset data using a navigated surgical system during the THA procedure, thereby obviating the need for these data to be calculated manually, e.g., by a surgeon or other medical professional, based on a known neck size.

BRIEF DESCRIPTION OF THE INVENTION

A first aspect of the disclosure provides a method of tracking one or both of a leg length or an offset in a patient during a total hip arthroplasty (THA) procedure, the method comprising: registering a pelvis of the patient to a navigated surgical system; measuring a native leg length of the patient using a navigated instrument; affixing an expandable trial femoral assembly to a prepared and broached femur of the patient; reducing the expandable trial femoral assembly into an acetabular prosthesis; and using a navigated driver, adjusting an expansion extent of the expandable trial femoral assembly; and measuring one or both of the leg length or the offset in the patient, wherein the navigated driver comprises a first reference element thereon, and a second reference element, wherein the second reference element is movable relative to the first reference element.

In certain embodiments, a distance moved by the second reference element relative to the first reference element is representative of one or both of the leg length or the offset of the patient.

In certain embodiments, the first reference element is a tracking array affixed to the navigated driver, and the second reference element comprises a length indicator disposed on a movable mount.

In certain embodiments, adjusting the expansion extent of the expandable trial femoral assembly further comprises actuating a knob of the navigated driver to expand or collapse the expandable trial femoral assembly.

In certain embodiments, registering the pelvis further comprises affixing a dynamic reference base (DRB) to the pelvis of the patient; and using the DRB to register the pelvis to the navigated surgical system.

In certain embodiments, the navigated instrument comprises a stylus having a tracking array disposed thereon.

In certain embodiments, the expandable trial femoral assembly comprises a head; a neck connected to the head; and a stem or broach connected to the neck, wherein the neck is expandable and collapsible.

A second aspect of the disclosure provides a method of tracking one or both of a leg length or an offset in a patient during a total hip arthroplasty (THA) procedure, the method comprising: registering a pelvis of the patient to a navigated surgical system; creating a checkpoint on a femur of the patient; measuring a native leg length of the patient, including contacting a navigated instrument to the checkpoint; affixing an expandable trial femoral assembly to the femur, wherein the femur is prepared and broached; reducing the expandable trial femoral assembly into an acetabular prosthesis; using a driver, adjusting an expansion extent of the expandable trial femoral assembly; and contacting the navigated instrument to the checkpoint on the femur to capture a measurement of the leg length or the offset.

In certain embodiments, the navigated instrument comprises a stylus having a tracking array disposed thereon.

In certain embodiments, creating the checkpoint further comprises using a checkpoint punch.

In certain embodiments, the navigated instrument contacts the checkpoint a plurality of times during the adjusting.

In certain embodiments, the plurality of times occurs intermittently throughout the adjusting.

In certain embodiments, adjusting the expansion extent of the expandable trial femoral assembly further comprises actuating a knob of the driver to expand or collapse the expandable trial femoral assembly.

In certain embodiments, registering the pelvis further comprises affixing a dynamic reference base (DRB) to the pelvis of the patient; and using the DRB to register the pelvis to the navigated surgical system.

In certain embodiments, the expandable trial femoral assembly comprises a head; a neck connected to the head;

and a stem or broach connected to the neck, wherein the neck is expandable and collapsible.

A third aspect of the disclosure provides a method of tracking one or both of a leg length or an offset in a patient during a total hip arthroplasty (THA) procedure, the method comprising: affixing a first reference element to a pelvis of the patient and, using the first reference element, registering the pelvis to a navigated surgical system; affixing a second reference element to a femur of the patient and, using the second reference element, registering the femur of the patient to the navigated surgical system; affixing an expandable trial femoral assembly to the femur, wherein the femur is prepared and broached; reducing the expandable trial femoral assembly into an acetabular prosthesis; using a driver, adjusting an expansion extent of the expandable trial femoral assembly; and using the navigated surgical system, tracking a movement of the second reference element relative to the first reference element, thereby tracking one or both of the leg length or the offset.

In certain embodiments, the first reference element is a first dynamic reference base (DRB) affixed to the pelvis of the patient.

In certain embodiments, the second reference element is a second dynamic reference base (DRB) affixed to the femur of the patient.

In certain embodiments, the expandable trial femoral assembly comprises a head; a neck connected to the head; and a stem or broach connected to the neck, wherein the neck is expandable and collapsible.

In certain embodiments, adjusting the expansion extent of the expandable trial femoral assembly further comprises actuating a knob of the driver to expand or collapse the expandable trial femoral assembly.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

Aspects of the present disclosure are illustrated by way of example and are not limited by the accompanying drawings. In the drawings:

FIG. 4 illustrates a block diagram of a surgical system that includes an extended reality headset, a computer platform, imaging devices, and a surgical robot, which are configured to operate according to some embodiments of the present disclosure.

FIG. 5 illustrates a flowchart of a workflow during an intra-operative portion of a total hip arthroplasty (THA) surgery, in accordance with some embodiments of the present disclosure.

FIG. 10 is a perspective view of a trial femoral neck from left to right in a first image of a contracted or collapsed neck position, a second image showing a potential neck expansion, and a third image of an expanded neck position.

FIG. 11 is a perspective view of a trial femoral neck from left to right in a first image of a standard position of the stem in relation to the neck, a second image showing the potential lateral offset of the stem, and a third image of a laterally shifted stem in relation to the neck.

FIG. 25 shows a process flow diagram for measuring leg length and offset, according to an embodiment of the disclosure.

Figure 1:
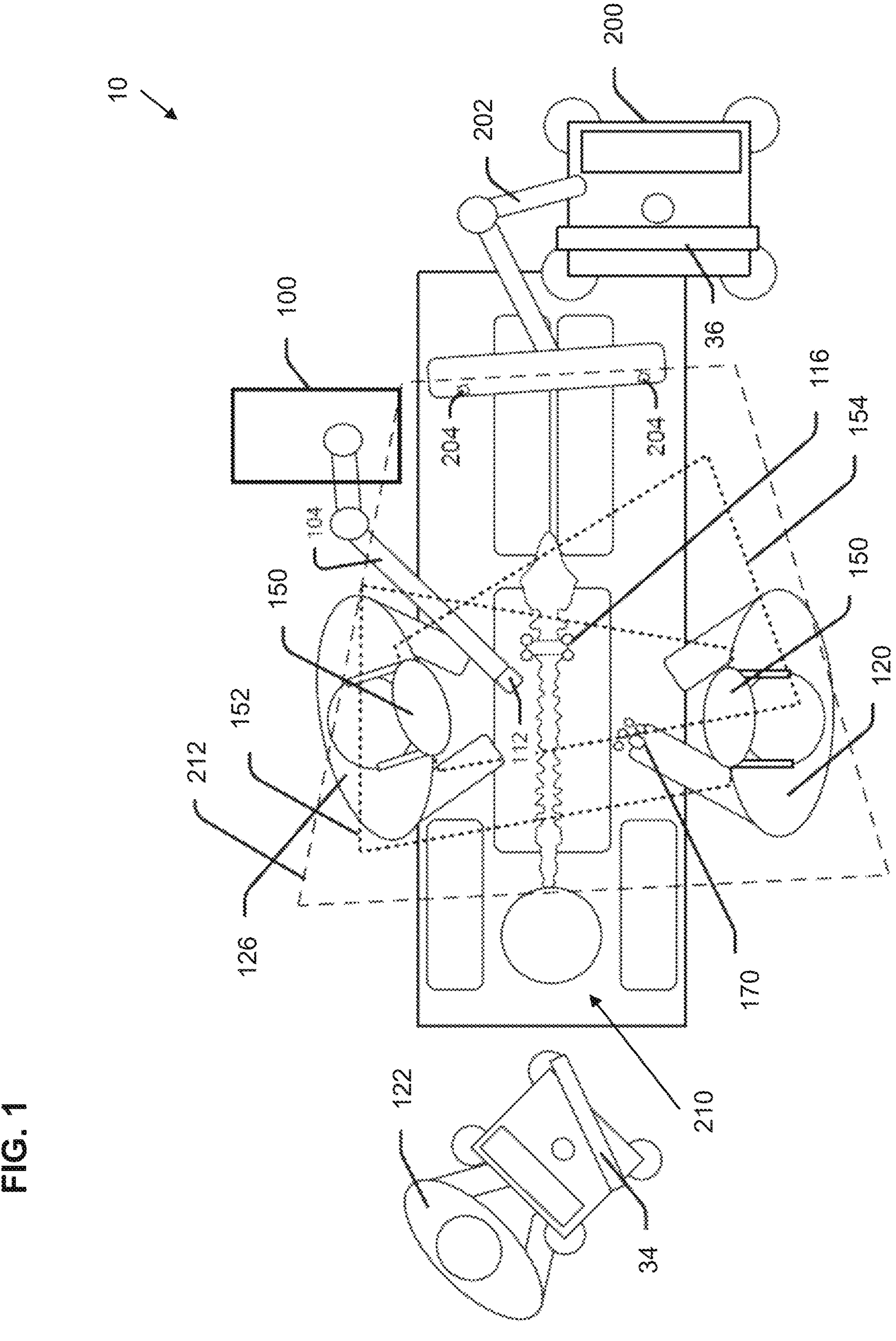
FIG. 1 is an overhead view of a surgical system arranged during a surgical procedure in a surgical room which includes a camera tracking system for computer assisted navigation during surgery, and a surgical robot for robotic assistance according to some embodiments of the present disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

Surgery systems including computer-assisted navigation capabilities are a well-established technique in operating rooms, including their use in arthroplasty procedures. Computer-assisted navigation systems provide surgeons with computerized visualization of how a surgical instrument or other device that is posed relative to a patient correlates to a pose relative to medical images of the patient's anatomy, and how those poses correlate to a pre-operative surgical plan. Camera tracking systems for computer assisted surgery navigation typically use a set of tracking cameras to track a pose of a reference element on the surgical instrument, which may be coupled to a surgical robot or may be operated freehand by a surgeon. In either case, the surgical instrument may be positioned by the surgeon during surgery, relative to a patient reference element (or "dynamic reference base" (DRB)) affixed to the patient. A computer model of a real instrument is associated with a reference element, so that the computer model can be overlaid on registered images of patient's anatomy. The camera tracking system uses the relative poses of the reference elements to determine how the real instrument is posed relative to the patient and to determine how the computer model of the real instrument is to be correspondingly posed as overlaid on the medical images. The surgeon can thereby use real-time visual feedback of the relative poses to navigate the surgical instrument during a surgical procedure on the patient.

The present application is related to (1) patent application Ser. No. 15/180,126, filed Jun. 13, 2016 (U.S. Pat. No. 10,842,453), (2) patent application Ser. No. 15/157,444, filed May 18, 2016 (U.S. Pub. No. 2016/0256225), (3) patent application Ser. No. 18/743,685, filed Jun. 14, 2024, (4) patent application Ser. No. 18/743,388, filed Jun. 14, 2024, (5) patent application Ser. No. 18/743,647, filed Jun. 14, 2024, (6) patent application Ser. No. 18/743,615, filed Jun. 14, 2024, (7) patent application Ser. No. 18/770,993, filed Jun. 14, 2024, and (8) patent application Ser. No. 18/770,993, each of which is incorporated herein by reference.

As noted above, a robotic system may be used for arthroplasty procedures. The robotic system (or, "robot" or "surgical robot") has a serial arm on which an end effector is mounted. The surgeon (or "user") may hold the end effector or any instruments coupled thereto, to perform surgical operations while watching in real time on a navigation system (e.g., on stand-alone display(s) or an Augmented Reality (AR) headset), and to receive various types of relevant feedback and information associated with a defined plan for and/or progress of the surgical procedure.

The serial arm can move through computer guided control to a suitable position for the surgery, e.g., pursuant to the surgeon's request, which may be provided via a foot pedal, touchscreen, AR interaction, etc. The passive robotic structure allows the surgeon to precisely perform each operation in the procedure.

Various workflows can be available for use with the system. Such workflows may incorporate preoperative scans or images of the patient (e.g., x-ray or Computerized Tomography (CT)). On the other hand, other workflows may be imageless, and may not require any pre-operative images. Some workflows may incorporate acquisition of intra-operative information about the patient anatomy. In one example, the surgeon may measure key parameters of the bone using a camera tracking system and an appropriate tracked instrument to capture points on patient anatomy. Later, this information, and other intra-operatively-acquired information may be used to plan the implant position and orientation with respect to patient anatomy, and to navigate the robot and surgical instruments during the surgical procedure.

In some workflows, the surgeon may rigidly attach a reference element to one or more bones, where the reference element includes fiducials which are detected by tracking cameras for computer assisted navigation. The reference elements allow tracking of bone position by the navigation system. The reference elements can be positioned on the bone and oriented such that they can be seen by the tracking cameras of the navigation system. Once positioned, the reference elements are attached with fixation structures (e.g., screw pins, "crocodile" jaws) on the bone (e.g., pelvis or femur). The reference elements' respective positions and orientations stay rigidly fixed with respect to the bone throughout the procedure.

Figure 2:
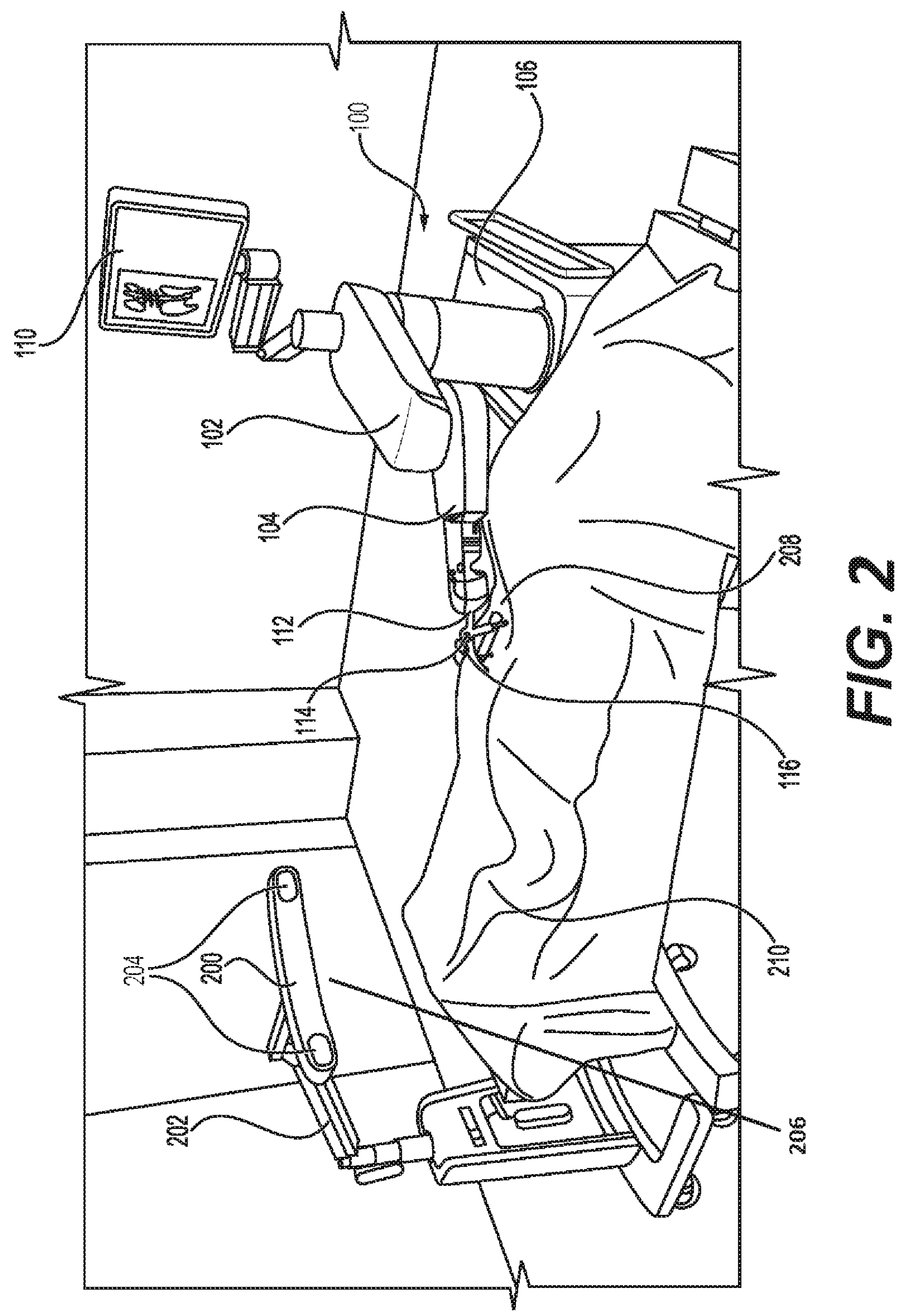
FIG. 2 illustrates the camera tracking system and the surgical robot of FIG. 1, positioned relative to a patient according to some embodiments of the present disclosure.
Figure 3:
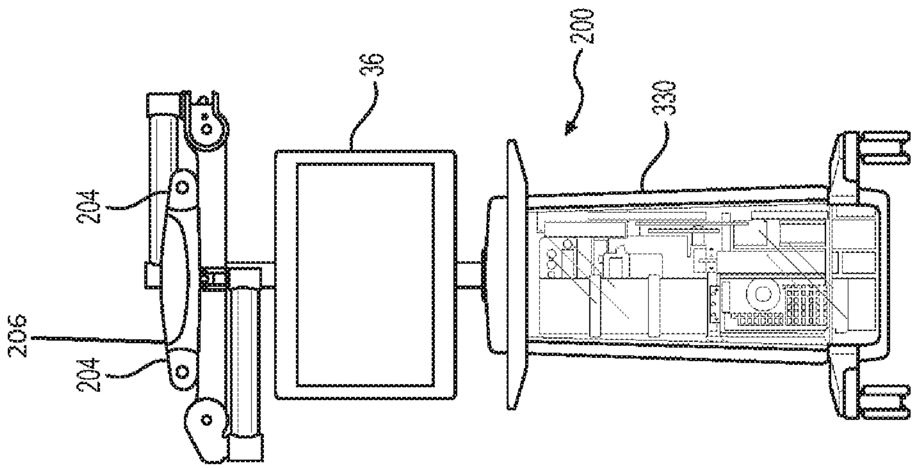
FIG. 3 further illustrates the camera tracking system and the surgical robot of FIGS. 1-2, configured according to some embodiments of the present disclosure.
Figure 3:
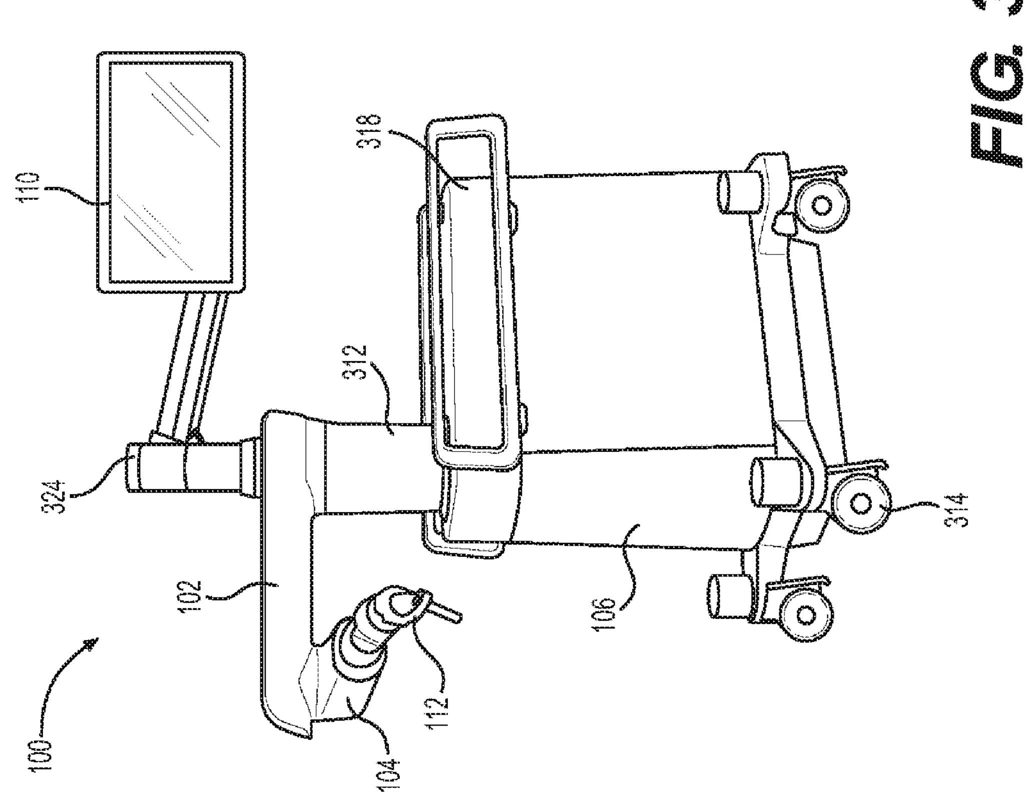

Turning to the figures, FIG. 1 is an overhead view of a surgical system 10 arranged during a surgical procedure in a surgical or operating room. The system 10 includes a camera tracking system 200 for computer assisted navigation during surgery and may further include a surgical robot 100 for optional robotic assistance according to certain embodiments. FIG. 2 illustrates the camera tracking system 200 and the surgical robot 100 positioned relative to a patient according to some embodiments. FIG. 3 further illustrates the camera tracking system 200 and the surgical robot 100 configured according to some embodiments. FIG. 4 illustrates a block diagram of a surgical system 10 that includes an extended reality (XR) headset 150, a computer platform 400, imaging devices 420, and the surgical robot 100 which are configured to operate according to some embodiments. In certain embodiments, the computer platform 400 including the camera tracking system 200 may be used in combination with the XR headset 150 and/or the imaging device(s) 420 to assist the surgeon in performing freehand procedures, i.e., use of the surgical robot 100 may be omitted.

The camera tracking system 200 (FIGS. 1-4) in some cases includes an intraoperative imaging system, that can include distinct imaging modalities. These imaging modalities may include one or more of fluoroscopy, 2D Radiography, and Cone-beam computed tomography (CBCT). Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (or, cone beam 3D imaging or C-arm CT), is a medical imaging technique consisting of X-ray computed tomography where the X-rays are divergent, forming a cone. The camera tracking system 200 is capable of: (1) capturing 3-Dimensional (3D) images (e.g., CT, CBCT, MCT, PET, Angiogram, MRI, ultrasound, etc.), (2) capturing 2-Dimensional (2D) images (e.g., fluoroscopy, digital radiography, ultrasound, etc.), and (3) containing an integrated or detachable navigation array having tracking markers (e.g., NIR retroreflective, NIR LED, visible, etc.), which is calibrated to the image space of the 2D and 3D images.

The surgical robot 100 is capable of: (1) using registered 2D and/or 3D images for surgical planning, navigation, and guidance in a variety of workflows (e.g., intraoperative 3D, intraoperative 2D, preoperative 3D to 2D, and intraoperative 3D to 2D, etc.); and (2) containing a camera tracking system 200 capable of tracking markers (e.g., NIR retroreflective, NIR LED, visible, etc.). In some cases, as noted herein, a dynamic reference base (DRB) (or patient reference array) 116 is (1) capable of rigidly attaching to the patient anatomy, and (2) contains an array of tracking markers (e.g., NIR retroreflective, NIR LED, visible, etc.).

The XR headsets 150 may be configured to augment a real-world scene with computer generated XR images while worn by personnel in the operating room. The XR headsets 150 may be configured to provide an augmented reality (AR) viewing environment by displaying the computer generated XR images on a see-through display screen that allows light from the real-world scene to pass therethrough for combined viewing by the user. Alternatively, the XR headsets 150 may be configured to provide a virtual reality (VR) viewing environment by preventing or substantially preventing light from the real-world scene from being directly viewed by the user while the user is viewing the computer-generated AR images on a display screen. The XR headsets 150 can be configured to provide both AR and VR viewing environments. Thus, the term XR headset encompasses both or either of an AR headset or a VR headset.

With continuing reference to FIGS. 1-4, the surgical robot 100 may include, for example, one or more robot arms 102, 104, a display 110, an end effector 112, for example, including a guide tube and an end effector reference element 114 which can include one or more tracking fiducials. A patient reference element (or DRB) 116 (shown in FIG. 1) has a plurality of tracking fiducials and is secured directly to the patient 210. For example, a navigated pelvis DRB marker array may be placed intra-incision or extra-incision with the help of cortical pins drilled into the pelvic bone. In some embodiments, the DRB is oriented to be visible by the tracking camera(s) 204 (e.g., a stereoscopic tracking camera) installed on the camera tracking system 200 and/or the XR headset 150. A reference element 170 is attached to or formed on an instrument, surgical tool, surgical implant device, etc.

The camera tracking system 200 includes tracking cameras 204 which may be spaced apart to provide stereo cameras configured with partially overlapping fields-of-view. The camera tracking system 200 can have any suitable configuration of arm(s) 202 to move, orient, and support the tracking cameras 204 in a desired location, and may contain at least one processor operable to track the location of an individual fiducial and pose of an array of fiducials of a reference element.

As used herein, the term "pose" refers to the location (e.g., along three orthogonal axes, e.g., the x-, y-, and z-axes) and/or the rotation angle (e.g., about the three orthogonal axes) of fiducials (e.g., DRB) relative to another fiducial (e.g., surveillance fiducial) and/or to a defined coordinate system (e.g., camera coordinate system, navigation coordinate system, etc.). A pose may therefore be defined based on only the multidimensional location of the fiducials relative to another fiducial and/or relative to the defined coordinate system, based on only the multidimensional rotational angles of the fiducials relative to the other fiducial and/or to the defined coordinate system, or based on a combination of the multidimensional location and the multidimensional rotational angles. The term "pose" therefore is used to refer to location, rotational angle, or combination thereof of, e.g., an instrument reference element 170, a patient reference element 116, or the like.

The tracking cameras 204 may include, e.g., infrared cameras (e.g., bifocal or stereophotogrammetric cameras) operable to identify, for example, active and passive tracking fiducials for single fiducials (e.g., a surveillance fiducial) and reference elements which can be formed on or attached to the patient 210 (e.g., patient reference element or DRB 116), end effector 112 (e.g., end effector reference element 114), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the fiducials in order to identify and determine locations of individual fiducials and poses of the reference elements in three-dimensions. For example, active reference elements may include infrared-emitting fiducials that are activated by an electrical signal (e.g., infrared light emitting diodes (LEDs)), and passive reference elements may include retro-reflective fiducials that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track the location of a surveillance fiducial and poses of reference elements within the XR camera headset fields of view (FOVs) 152 and 154, respectively. Accordingly, as illustrated in FIG. 1, the location of the surveillance fiducial and the poses of reference elements on various objects such as, e.g., instrument reference element 170 and patient reference element 116, can be tracked while in the FOVs 152 and 154 of the XR headsets 150 and/or a FOV 212 of the tracking cameras 204.

FIGS. 1 and 2 illustrate a potential configuration for the placement of the camera tracking system 200 and the surgical robot 100 in an operating room environment. Computer assisted navigated robotic surgery can be provided by the surgical robot 100, the camera tracking system 200 controlling the XR headsets 150 and/or other displays 34, 36, and 110 to display surgical procedure navigation information.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100), imaging devices 420 (FIG. 4), remote sources (e.g., patient medical image database), and/or other electronic equipment. The camera tracking system 200 may track fiducials in 6 degrees-of-freedom (6 DOF) relative to three axes of a 3D coordinate system and rotational angles about each axis. The XR headsets 150 may also operate to track hand poses and gestures to enable gesture-based interactions with "virtual" buttons and interfaces displayed through the XR headsets 150, and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar 206 supports the tracking cameras 204 and may include a color camera. The machine vision navigation bar generally has a more stable view of the environment because it does not move as often or as quickly as the XR headsets 150 while positioned on wearers' heads. The patient reference element (or, DRB) 116 is generally rigidly attached to the patient 210 with stable pitch and roll relative to gravity. This local rigid patient reference 116 can serve as a common reference for reference frames relative to other tracked elements, such as a reference element 114 on the end effector 112, instrument reference element 170, and reference elements on the XR headsets 150.

In some embodiments, at the end of the end effector 112, instruments are connected to perform operations such as resection, reaming, broaching, and implant placement and adjustment.

The surgical robot 100 may be positioned near or next to patient 210 as shown in FIGS. 1-2. The robot 100 can be positioned at any suitable location near the patient 210 depending on the area of the patient 210 undergoing the surgical procedure. The camera tracking system 200 may be separate from the robot system 100 and positioned at the foot of patient 210. This location allows the tracking camera 200 to have a direct visual line of sight to the surgical area 208, e.g., the hip area (FIG. 2). In the configuration shown in FIG. 1, the surgeon 120 may be positioned across from the robot 100, but is still able to manipulate the end effector 112 and the display 110. A surgical assistant 126 may be positioned across from the surgeon 120 again with access to both the end effector 112 and the display 110. If desired, the locations of the surgeon 120 and the assistant 126 may be reversed. An anesthesiologist 122, nurse, or scrub tech can operate equipment which may be connected to display information from the camera tracking system 200 on a display 34 (FIG. 1).

With respect to the other components of the robot 100, the display 110 can be attached to the surgical robot 100 or in a remote location. The end-effector 112 may be coupled to the robot arm 104 and be controlled by at least one motor. An upper arm 102 may further couple the arm 104 to the column 312 of the robot 100. In some embodiments, the end effector 112 includes a guide tube which is configured to receive and orient a surgical instrument, tool, or implant used to perform a surgical procedure on the patient 210. For example, the end effector 112 is adapted to receive (e.g. through a guide tube) a surgical instrument or a portion thereof, to removably couple to the instrument, and to manipulate the instrument such as by translating and rotating the instrument. In some other embodiments, the end-effector 112 includes a passive structure guiding a saw blade (e.g., sagittal saw) along a defined cutting plane.

As used herein, the term "end effector" is used interchangeably with the terms "end effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term, device, can also refer to structure of the end effector, etc. Example instruments, tools, and implants include, without limitation, reamer constructs, drills, screwdrivers, saws, dilators, retractors, probes, implant inserters, and implant devices such as shells and trial shells, screws, spacers, interbody fusion devices, plates, rods, etc. It will be appreciated that the end-effector 112 may be replaced with any suitable instrumentation for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axes, and a Z Frame axis, such that one or more of the Euler Angles (e.g., roll, pitch, and/or yaw) associated with the end effector 112 can be selectively computer controlled. In some embodiments, selective control of the translation and orientation of end effector 112 and associated surgical instrument can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headset(s) 150 can be controlled to dynamically display an updated graphical indication of the pose of the surgical instrument so that the user, e.g., surgeon 120, can be aware of the pose of the surgical instrument at all times during the procedure.

In some further embodiments, surgical robot 100 can be operable to correct the path of a surgical instrument guided by the robot arm 104 if the surgical instrument strays from the selected, preplanned, or defined trajectory. The surgical robot 100 can be operable to permit stoppage, modification, and/or manual control of the movement of end effector 112 and/or the surgical instrument. Thus, in use, a surgeon 120 or other user can use the surgical robot 100 as part of computer assisted navigated surgery, and has the option to stop, modify, or manually control the autonomous or semi-autonomous movement of the end-effector 112 and/or the surgical instrument.

Fiducials of reference elements can be formed on or connected to robot arms 102 and/or 104, the end effector 112 (e.g., end effector element 114 in FIG. 2), and/or a surgical instrument (e.g., instrument element 170) to enable tracking of poses in a defined coordinate system, e.g., such as in six degrees of freedom (DOF) along three orthogonal axes and rotation about the axes. The reference elements 114, 116, 170 enable each of the marked objects (e.g., the end-effector 112, the patient 210, and the surgical instruments, respectively) to be tracked by the tracking camera 200, and the tracked poses can be used to provide navigated guidance during a surgical procedure and/or to control movement of the surgical robot 100 for guiding the end effector 112 and/or an instrument manipulated by the end effector 112. The instrument manipulated by the end effector 112 may include, e.g., a reamer, an inserter adapted to insert an implant, a driver, and so on.

Referring to FIG. 3 the surgical robot 100 may include a display 110, upper arm 102, lower arm 104, end effector 112, vertical column 312, casters 314, a table 318, and ring 324 which uses lights to indicate statuses and other information. Cabinet 106 may house electrical components of surgical robot 100 including, but not limited to, a battery, a power distribution module, a platform interface board module, and a computer. The camera tracking system 200 may include a display 36, tracking cameras 204, arm(s) 202 (FIG. 1), a computer housed in cabinet 330, and other components.

In computer assisted navigated surgeries, perpendicular 2D scan slices, such as axial, sagittal, and/or coronal views of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 4 illustrates a block diagram of a surgical system 10 that includes a surgical robot 100, a computer platform 400 including, inter alia, the camera tracking system 200, imaging device(s) 420, and XR headset(s) 150 which are configured to operate as described herein, according to some embodiments.

The imaging device(s) 420 may include a C-arm imaging device, an O-arm imaging device, other imaging device, and/or a patient image database of 2D and/or 3D images. The XR headset 150 provides a human interface for performing navigated surgical procedures. The XR headset 150 can be configured to provide functionalities, e.g., via the computer platform 400, that include without limitation any one or more of: identification of hand gesture-based commands, and display of XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field-of-view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, the surgical system 10 includes the camera tracking system 200 which may be connected to a computer platform 400 for operational processing and which may provide other operational functionality including a navigation controller 404 and/or an XR headset controller 410. The surgical system 10 may further include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector 112 of the surgical robot 100. The navigation information may be displayed through the display device 438 of the XR headset 150 and/or another display device to indicate where the surgical tool and/or the end effector 112 of the surgical robot 100 should be moved to perform a surgical procedure according to a defined surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the O-arm imaging device, other imaging device(s), the patient image database, and/or to other medical equipment through the wired/wireless interface 440.

The surgical system 10 may include a XR headset controller 410 that at least partially resides in the XR headset 150, the computer platform 400, and/or another system component connected via wired cables and/or wireless communication links. Various functionality may be provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from the cameras 430 (tracking cameras), signals from the microphone 432, and/or information from the pose sensor 436 and the gesture sensor 434, to generate information for display as XR images on the display device 438 and/or for display on other display devices for user viewing. Thus, the XR headset controller 410 as illustrated as a circuit block within the XR headset 150 is to be understood as being operationally connected to other illustrated components of the XR headset 150 but not necessarily residing within a common housing or being otherwise transportable by the user. For example, the XR headset controller 410 may additionally or alternatively reside within the computer platform 400 which, in turn, may reside within the cabinet 330 of the camera tracking system 200, the cabinet 106 of the surgical robot 100, etc.

Exemplary Patient Registration Workflows

Another process of various workflows is to register the patient in the tracking space of the navigation system. Patient registration can include matching the patient anatomy with a numeric representation of the corresponding bone, such as a three-dimensional (3D) model of the bone. The bone representation may be constructed from, e.g., a set of CT images (CT workflow), a set of fluoroscopy images, or based on a generic bone model (imageless workflow). In some embodiments of the present disclosure, the system 10, e.g., computer platform 400, may perform one of a number of available workflows to register a patient to the surgical system 10 prior to surgery. The workflows may further include isolating a target area for the surgical procedure from non-target surgical areas.

In one embodiment, the workflow may be an imageless workflow in which no pre-operative images are used. Instead, information about the patient anatomy in the operating room (OR) can be obtained by the surgeon measuring key parameters of the patient's bone using the system as described herein. For example, the computer platform 400 of the system 10 operates to identify the locations of landmarks (e.g., points, axes, and/or surfaces) on the bone and register the locations either concurrently with the identification or thereafter. The locations can be used to define reference plane(s) (e.g., anterior pelvic plane (APP) and/or functional pelvic plane (FPP)) (FIG. 9) which, in turn, are used to plan implants and navigate the robot and surgical instruments for THA surgical procedures.

In some embodiments, the imageless workflow may be used in the initial patient assessment. For example, the surgeon may assess the patient's mobility and health status with assistance from sensors (e.g., sensors made by Globus Medical which are attached to the leg), physical exercises, and/or clinical surveys to determine if THA is recommended. Gathered data may then be stored and processed by the system before being analyzed by the surgeon to facilitate a final decision. Subsequently, the data may be reused by an application (e.g., surgery planning application by Globus Medical) to establish the most appropriate implant surgical plan.

Figure 5:
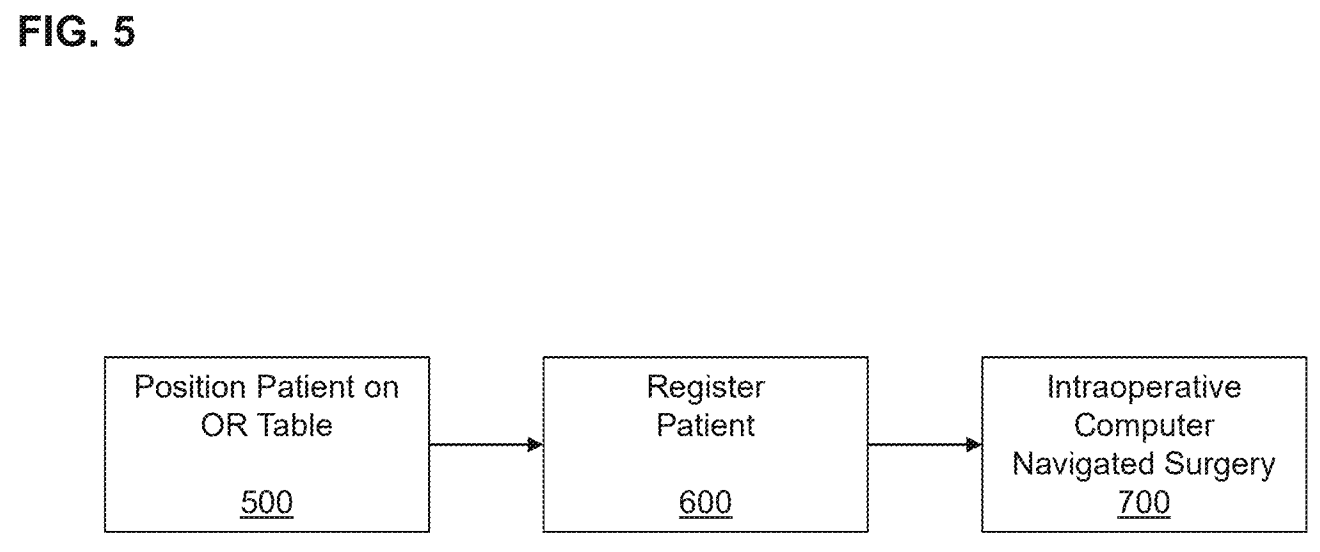

FIG. 5 illustrates a flowchart for an imageless workflow during an intra-operative portion of a THA surgery, in accordance with some embodiments of the present disclosure. In some embodiments, after positioning the patient on the operating room table (process 500), some of the operations discussed above and below may be performed during process 600 to register a patient and before another process 700 for intraoperative computer navigated surgery. In the case of a hip, a pelvis or acetabulum of the patient is registered in the tracking coordinate system of the camera tracking system 200. As shown in FIG. 1, the pelvis or acetabulum is registered in the optical coordinate system. In one embodiment, the registration is done in an imageless modality without the use of any medical images such as X-rays or CT images from an imaging device. As noted herein, in other embodiments, registration is performed using one or more pre-operative X-ray images and/or CT images.

Figure 6:
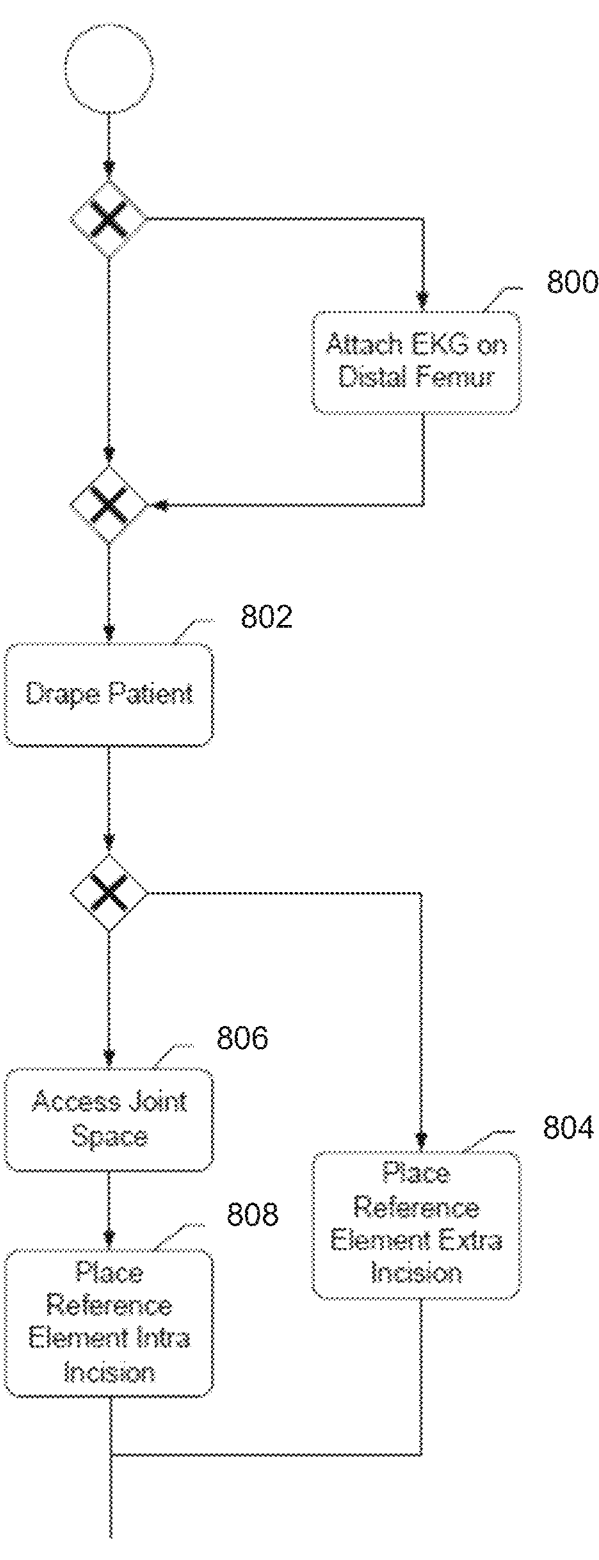
FIG. 6 illustrates a flowchart of a patient preparation process before registration, in accordance with some embodiments of the present disclosure.

FIG. 6 illustrates a flowchart of a patient preparation process before registration, in accordance with some embodiments of the present disclosure.

The patient preparation process may begin with a patient being positioned in a lateral or supine position on the OR table. The patient's body is prepared for registration. Optionally, in process 800, an EKG/ECG patch electrode is attached on or adjacent a distal end of the patient's femur. The EKG/ECG patch electrode may be placed on the center of the patella or slightly inferior to the center. In some embodiments, the patch location is in line with the anatomic axis of the femur. This patch may be used to acquire the most distal point of the femur under the drape at a later stage. This patch may also be used to track the femur in space (e.g., when the patient's leg is moved during surgery) and may also be used to assist in measuring the patient's leg length. However, in some embodiments, this operation (process 800) is skipped.

In some embodiments, the EKG/ECG patch electrode includes an adhesive patch that is removably attachable to the patient. In some embodiments, the patch may be black or dark to be more visible to the tracking camera. In other embodiments, the patch and patch electrodes are not visible by the tracking camera as they are under a drape. The patch geometry (like a nipple) will help the surgeon to always touch a single point on or adjacent the distal part of the femur (anterior patella region) with a navigated stylus/instrument which is trackable by the tracking camera. This ensures that the surgeon always collects the same point to measure the leg length or medio-lateral offset.

In process 802, the patient body is draped. Then, depending on the surgeon's technique, the navigated pelvis DRB is placed intra-incision (processes 806-808) or extra-incision (process 804) with the help of cortical pins drilled into the pelvic bone. In some embodiments, the DRB is oriented to be visible to the tracking camera(s), e.g., a stereoscopic tracking camera installed on the camera tracking system 200 (FIG. 1) or the XR headset 150 (FIG. 1). In one embodiment, the operation to place the DRB intra-incision, includes using the system to track and navigate access to the joint space (process 806) and placing the reference element intra-incision. In an alternative embodiment, the reference element is placed extra-incision (process 804) and the system does not necessarily need to be used to track and navigate access to the joint space.

After the reference element or DRB has been placed intra-incision or extra-incision, data points and axes can be collected on the patient anatomy with the assistance of navigated instruments and using the pelvis DRB coordinate system as a spatial reference. In addition to this, two pelvic reference planes can be established to plan placement of implants by measuring angular deviations such as inclination and version of the acetabular cup implant as shown in FIGS. 7-8.

Figure 7:
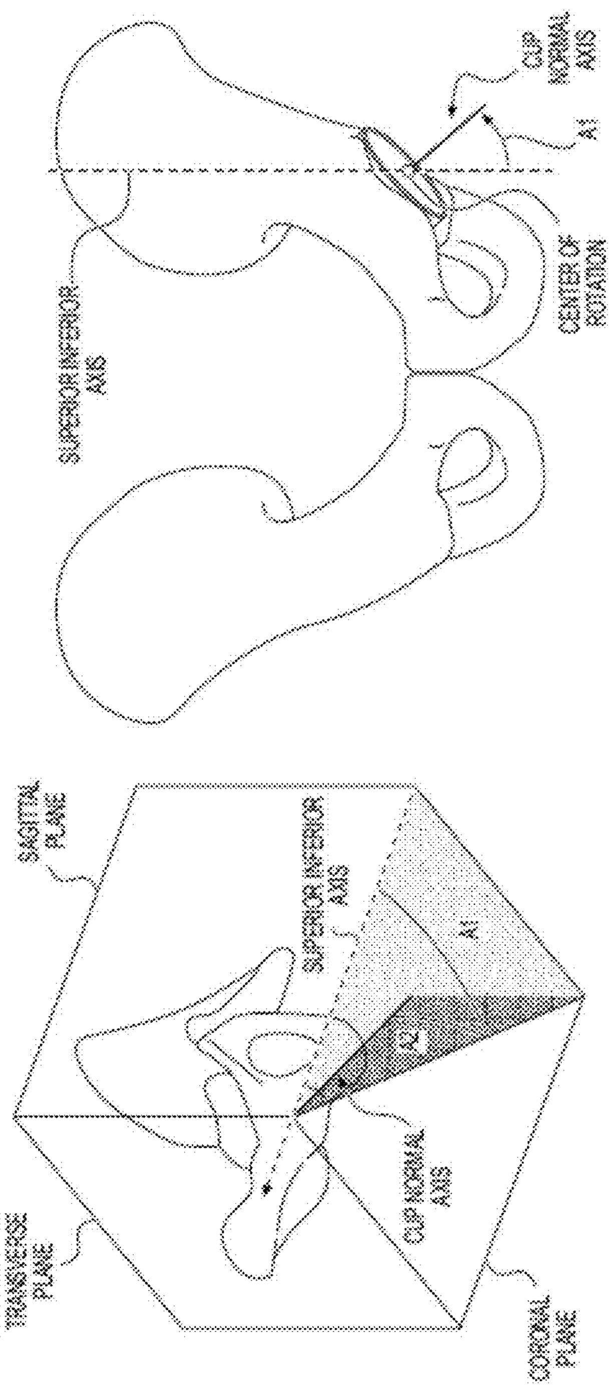
FIG. 7 illustrates a radiographic inclination angle measured in the coronal plane of the patient, in accordance with some embodiments of the present disclosure.
Figure 8:
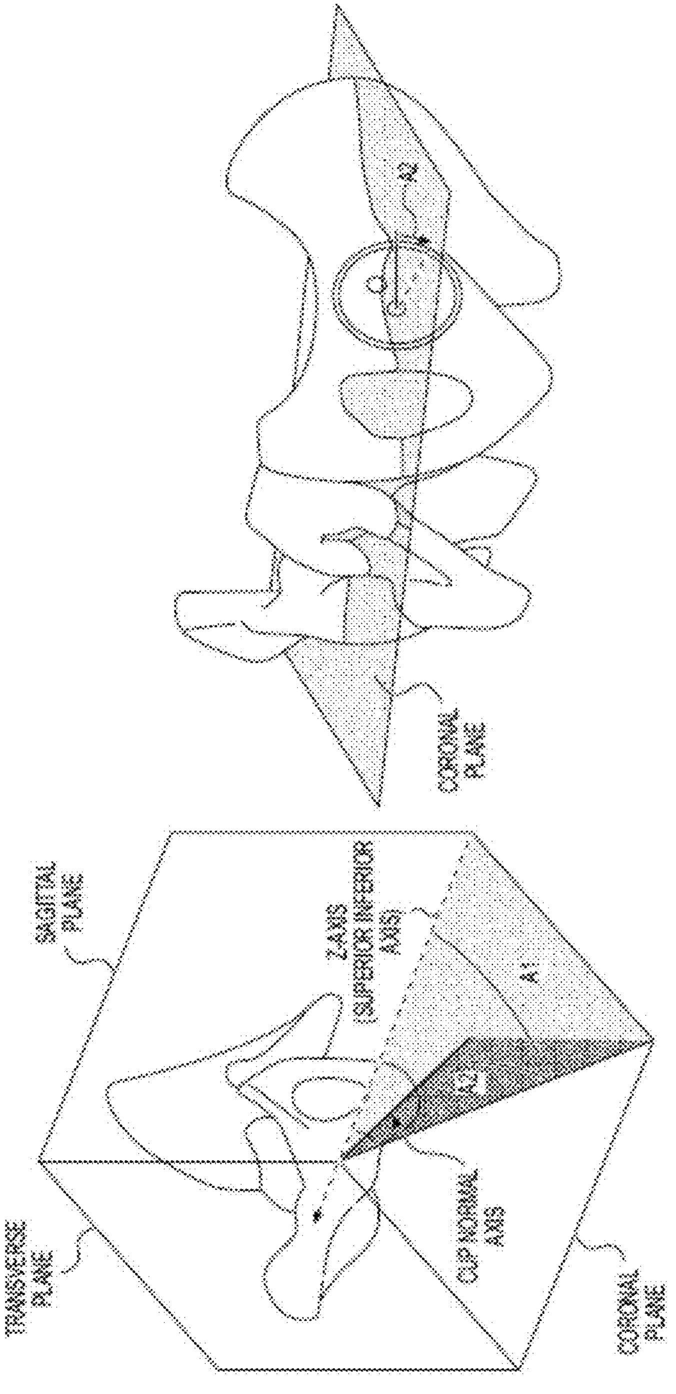
FIG. 8 illustrates a radiographic version angle measured relative to the coronal plane of the patient, in accordance with some embodiments of the present disclosure.

FIG. 7 illustrates a radiographic inclination angle measured in the coronal plane of the patient, in accordance with some embodiments of the present disclosure. In some embodiments, the surgeon may use a navigated instrument to palpate or paint the surface of the acetabular cavity of the patient to determine a center of rotation of the acetabulum. FIG. 8 illustrates a radiographic version angle measured relative to the coronal plane of the patient, in accordance with some embodiments of the present disclosure. The two pelvic reference planes (or coronal or frontal planes), the anterior pelvic plane (APP) and functional pelvic plane (FPP), are determined or defined using different landmarks and axes as shown on FIG. 9.

It is to be understood herein that although the user interfaces and associated operations are described as being performed in a certain sequence, they may be performed in other sequences while still being within disclosed embodiments. Moreover, it is not necessary that all of the user interfaces and/or described operations be performed. Instead, fewer operations may be performed while still being within disclosed embodiments. Further, additional registration approaches can include image-based and imageless workflows. Combinations of these registration approaches are also possible in keeping with the various disclosed embodiments.

Figure 9:
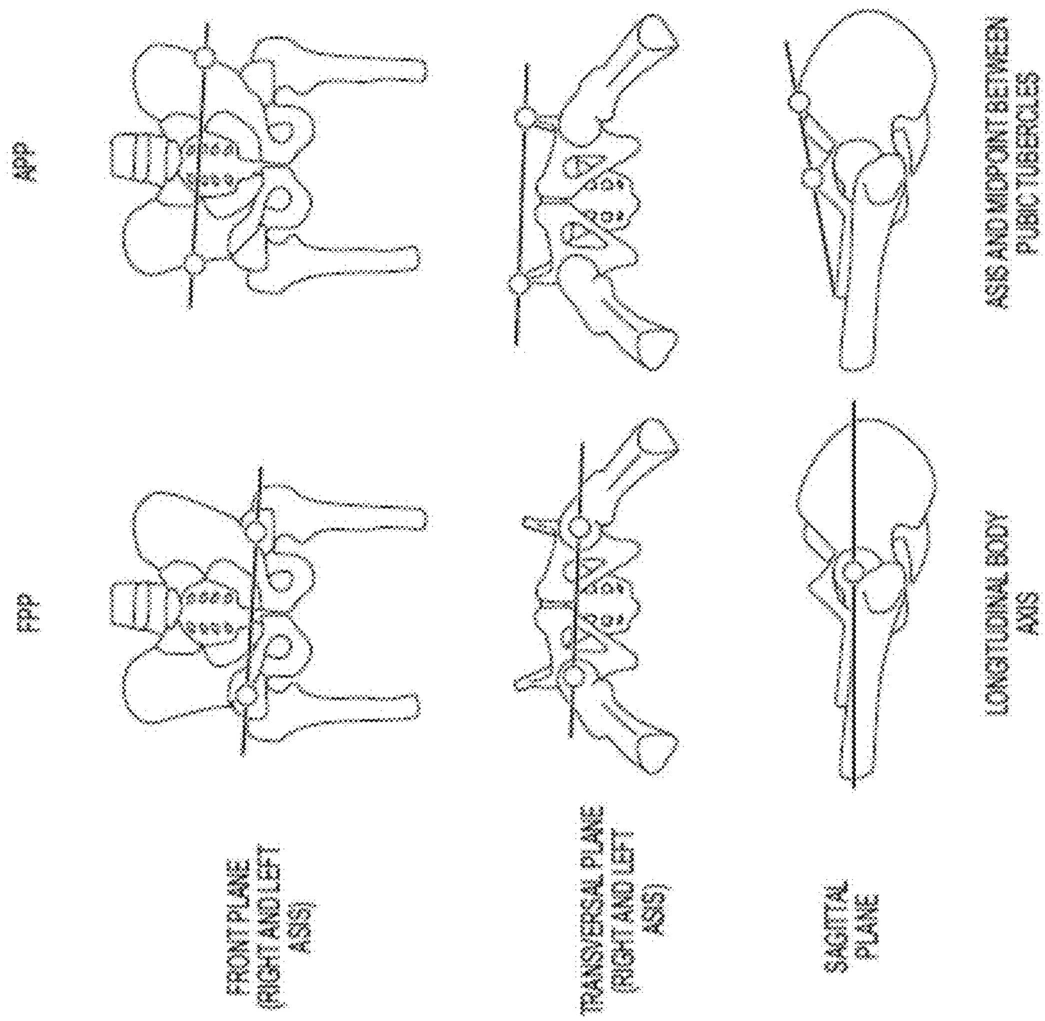
FIG. 9 illustrates different views of landmarks and axes for registration of a functional pelvic plane (FPP) and an anterior pelvic plane (APP) of a patient, in accordance with some embodiments of the present disclosure.

During a patient registration procedure, landmarks used to register patient anatomy can be extracted using either single point palpation collection or surface painting (resulting in a point cloud of locations). FIG. 9 illustrates different views of landmarks and axes for registration of the FPP and APP of a patient, in accordance with some embodiments of the present disclosure. The landmarks and axes used to register the APP and FPP planes are described in more detail in U.S. patent application Ser. No. 18/430,077, previously incorporated by reference herein.

Further, U.S. patent application Ser. No. 18/430,077 discloses processes for registration of a pelvic acetabulum of a patient (including painting the acetabular cavity), in accordance with various embodiments of the present disclosure. For example, to define the APP and FPP origins, the pelvic acetabular center of rotation can be determined after removing the femoral head of the patient from the acetabular cavity. The acetabular cavity may be made accessible by cutting the femoral neck and by removing the femoral head from the acetabular cavity. In some embodiments, a cork screw instrument may be used to remove the femoral head from the acetabular cavity.

The surface of the acetabular cavity can then be painted using the navigated instrument (e.g., a stylus). For example, the surgeon may use the navigated instrument (e.g., stylus) to palpate the surface of the acetabular cavity, as the tracking camera measures the position of a ball on the end of the stylus in a continuous way. This process provides a cloud of points for the measured positions (locations). At the same time, the tracking camera may also monitor and track the pose of the patient DRB 116 attached to the pelvis such that the pose of the stylus can be tracked relative to the pose of the patient DRB. Alternatively, the surgeon may subsequently measure a predefined number or percentage of points by palpating them one-by-one. Based on these points and the tracking data of the stylus and patient DRB 116, the center of rotation of the pelvic acetabular cavity is determined. Additionally, based on these points, the surface of the acetabular cavity may be registered in the system and/or a 3D model may be generated or modified based on these points. Next, the acetabular cavity shape can be recreated (e.g., in a 3D model) by the system based on the measured cloud of points and using other algorithms, e.g., for outlier removals and surface fitting.

While certain imageless approaches are described herein and in U.S. patent application Ser. No. 18/430,077, previously incorporated by reference herein, other example methods of performing imageless and image-based registration of the pelvis to the tracking coordinate system of the tracking system (e.g. optical coordinate system). These methods may also be used to, e.g., determine a native center of rotation of the acetabulum, derive or define an FPP, and derive or define an APP. Registration may allow a navigation system or robotic system to track any navigated instrument or end effector 112 or any tool attached to the end effector 112 relative to the pelvis as tracked by a patient dynamic reference base 116 attached to the pelvis. Various registration methods described herein can be combined in keeping with various disclosed embodiments.

For example, in one imageless method, an APP is derived by either touching various known points (e.g., left and right anterior superior iliac spine (ASIS) and pubic symphysis) with a navigated instrument, or by a physician lining up a plane or axis defined by the navigated instrument along or parallel to the APP. With the center of rotation and APP determined, the system (either a navigation system or a combined navigation and robot system 100) has sufficient information to register the acetabulum in the coordinate system (e.g., optical coordinate system) of the camera tracking system 200. In both of the above-noted example methods, the tracking system may be constantly monitoring and tracking the pose of the patient DRB 116 attached to the pelvis while also tracking the navigated instrument (e.g., stylus) such that the pose of the instrument can be tracked relative to the pose of the patient DRB, at least for purposes of registering the pelvis relative to the patient DRB 116 in the tracking coordinate system of the camera tracking system 200.

Some exemplary image-based examples include the use of pre-operative CT images, intra-operative fluoroscopy images, and intra-operative point cloud data acquired via a navigated instrument, as described in patent application Ser. No. 18/743,388, and patent application Ser. No. 18/743,615. Other exemplary image-based registration approaches can be performed using intra-operative fluoroscopy images, as described in patent application Ser. No. 18/743,647. In a further exemplary image-based approach to patient registration, intra-operative fluoroscopy images and intra-operative point cloud data acquired using a navigated instrument may be used, as described in patent application Ser. No. 18/743,685.

Computer-assisted navigation systems provide surgeons with computerized visualization of how a surgical instrument or other device that is posed relative to a patient correlates to a pose relative to medical images of the patient's anatomy, and how those poses correlate to a pre-operative surgical plan.

Expandable Trial Femoral Assembly

Expandable trial femoral assemblies such as, e.g., expandable trial femoral assembly 900, may be used in workflow described herein above, and may offer certain advantages such as, e.g., the ability to assess proper component position, joint stability, range of motion, and leg length, and to adjust one or more dimensions of the trial femoral assembly without dislocating the joint.

Figure 10:
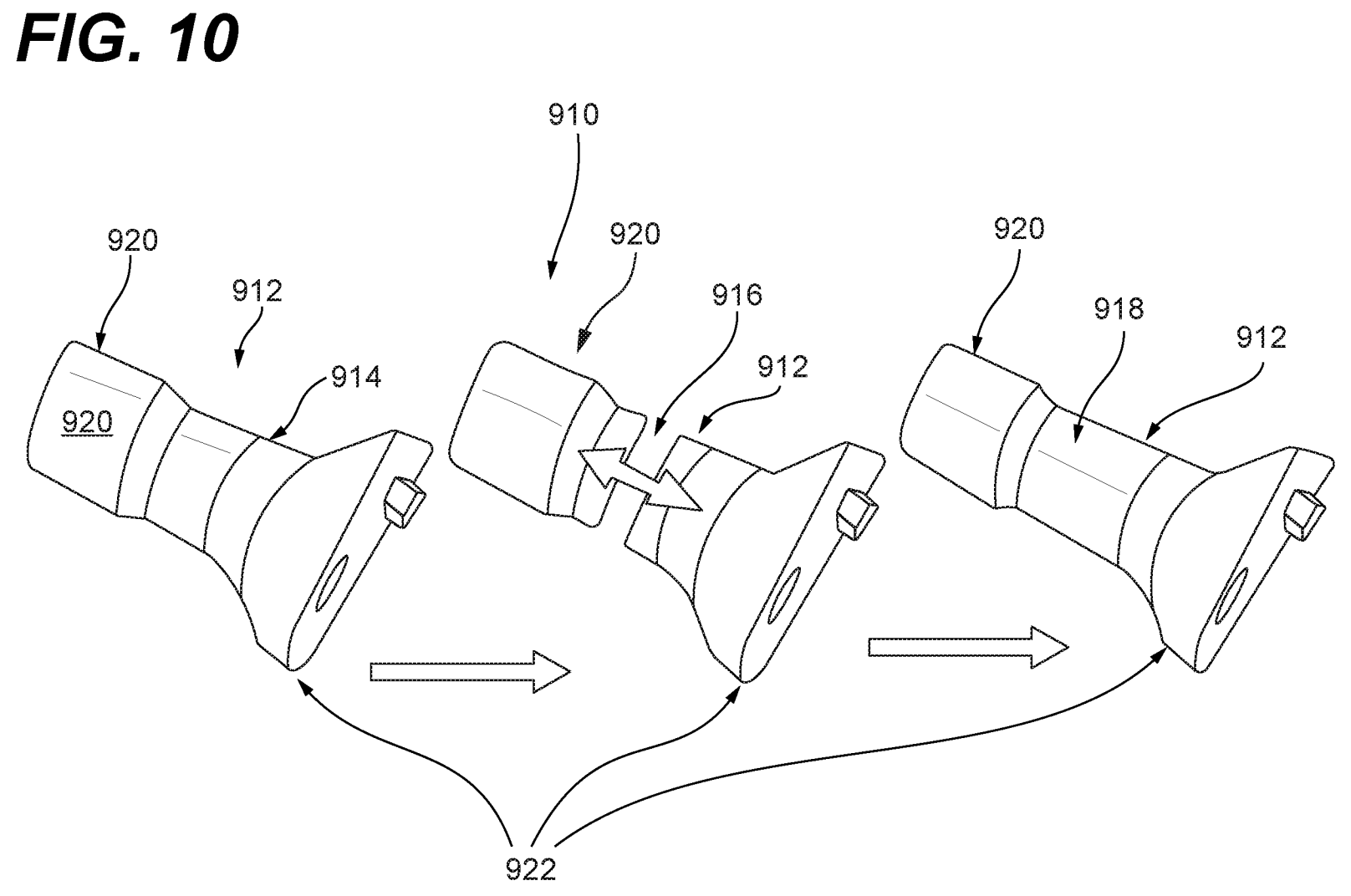

Referring now to FIG. 10, a trial femoral head and neck assembly is generally indicated by the numeral 910. The adjustable femur neck portion 912 of the trial femoral head and neck assembly 910 can adjust from standard to lateralized, and/or could expand over a range of sizes of trial trunnion 920. Moreover, the adjustable femur neck portion 912 can expand over a range of sizes that allows the surgeon to adjust the neck portion 912 while just using one neutral (+0 mm) trial head and would allow the surgeon to easily change the offset while the patient's joint is still reduced. The expansion mechanism of the adjustable femoral neck portion 912 will be on the internal portion of the adjustable femoral neck portion 912. It will be controlled by a separate instrument that the surgeon could turn with a click, indicating that it has adjusted to a new size. Trial trunnion 920 sizes range from −5 mm to +12 mm, so ideally, the trial femoral neck 920 will be able to expand throughout that entire range. There is a stem 922 for attachment to the femur. There can be a broach representative of the final stem implant geometry substituted for the stem 922. There is a first length 914 of the adjustable femur neck portion 912, a visual depiction of the expansion of neck portion along the neck axis 916 of the adjustable femur neck portion 912, and a second length 918 of the adjustable femur neck portion 912. The images in FIG. 10 show how the adjustable femoral neck portion 912 will expand along the axis 916 of the neck to lengthen. Such lengthening may be performed in increments so that the user can easily assess the extent of neck expansion. In certain embodiments, the neck portion may be laser marked to show the exact dimension.

Figure 11:
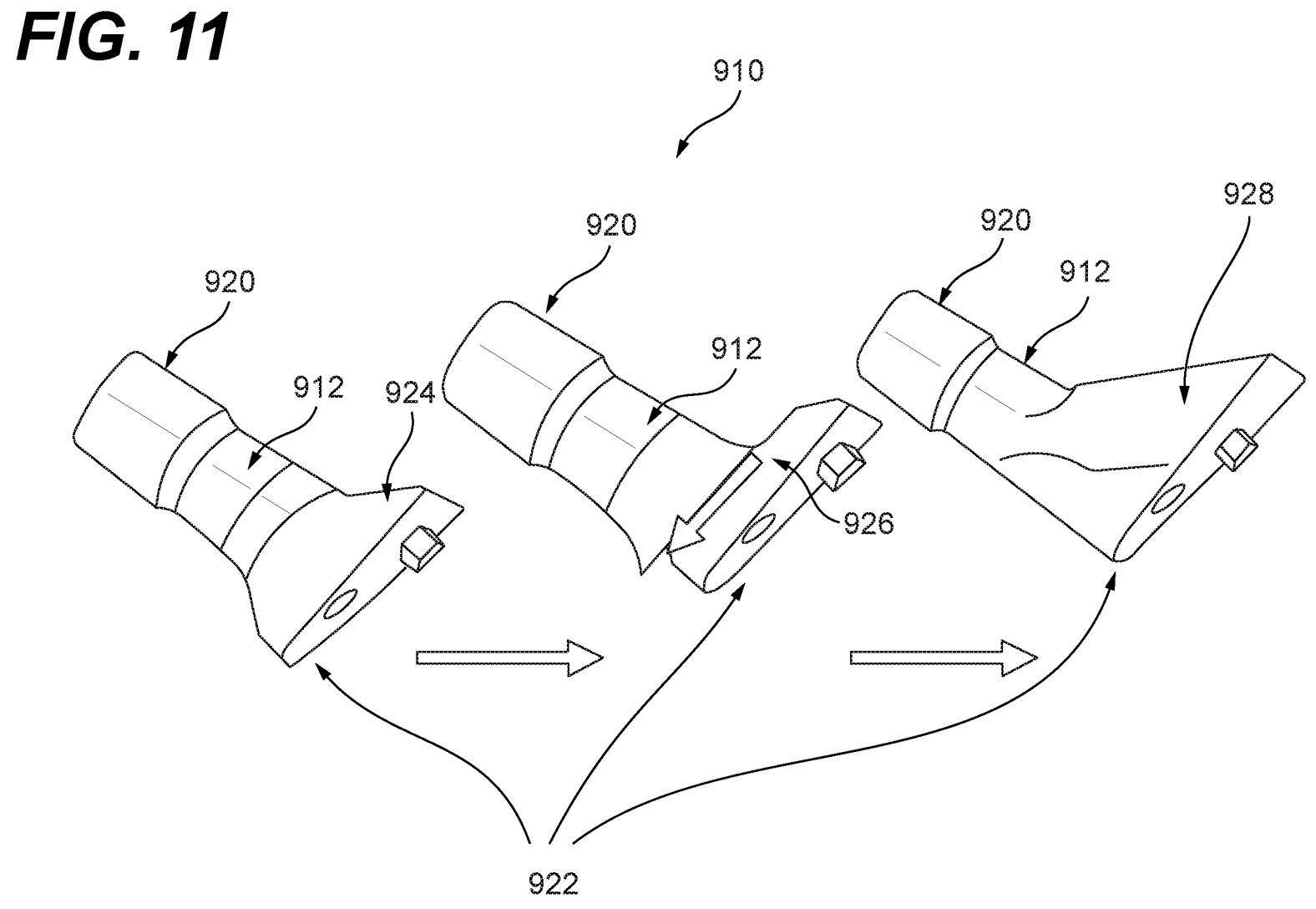

Referring now to FIG. 11, in certain embodiments, the trial femoral head and neck 910 may be adjustable so that a change from standard to lateralized can be accomplished. Currently, THA procedures utilize six total trial necks, including one standard and one lateralized trial neck for each three different neck lengths. The use of an adjustable femoral neck portion 912 capable of adjustment to be lateralized, reduces the total number of trial necks from six to three SKUs, each having a different neck length. As shown, stem 922 is adjustable between a standard position 924 of the stem 922 in relation to the adjustable femoral neck portion 912, as shown by a lateral change of stem 926 in relation to the adjustable femoral neck portion 912, to a lateralized position 928 of the stem 922 relative to the adjustable femoral neck portion 912. The trunnion 920 can be moved back and forth and could click into the correct place so that the user obtains tactile feedback to verify that the adjustable femoral neck portion 912 is located in the proper position. Preferably, there would be a visual indication showing the level of offset.

Figure 12:
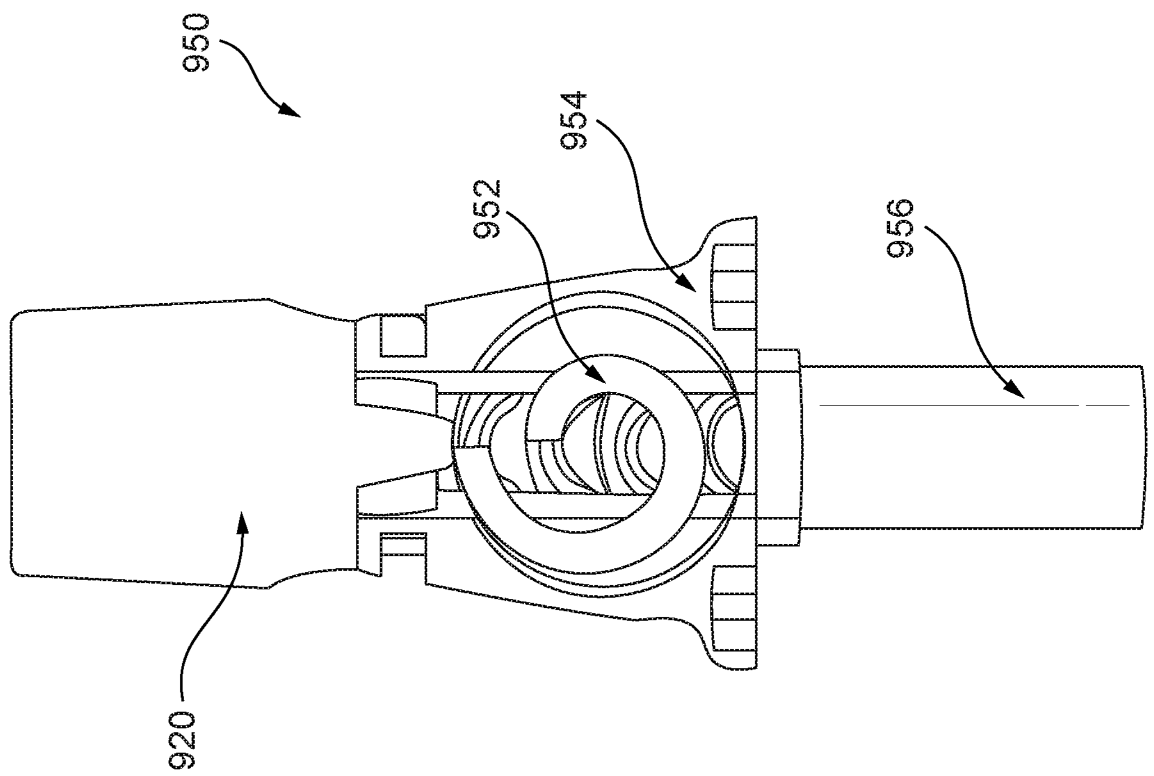
FIG. 12 is a front view of a first embodiment of a neck expansion and contraction mechanism trial femoral neck with a cutaway view within a housing that includes a tilted spiral cam.
Figure 13:
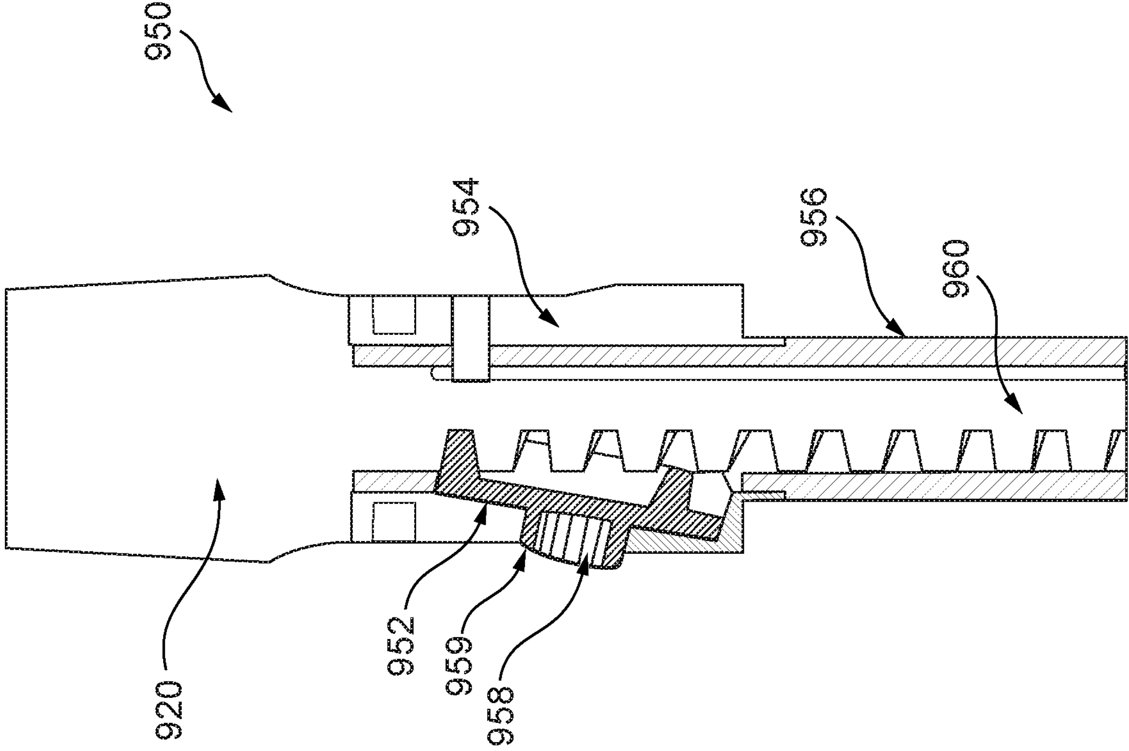
FIG. 13 is a side view of a first embodiment of a neck expansion and contraction mechanism trial femoral neck with a cutaway view of a notched rod interacting with the tilted spiral cam shown in FIG. 12.
Figure 14:
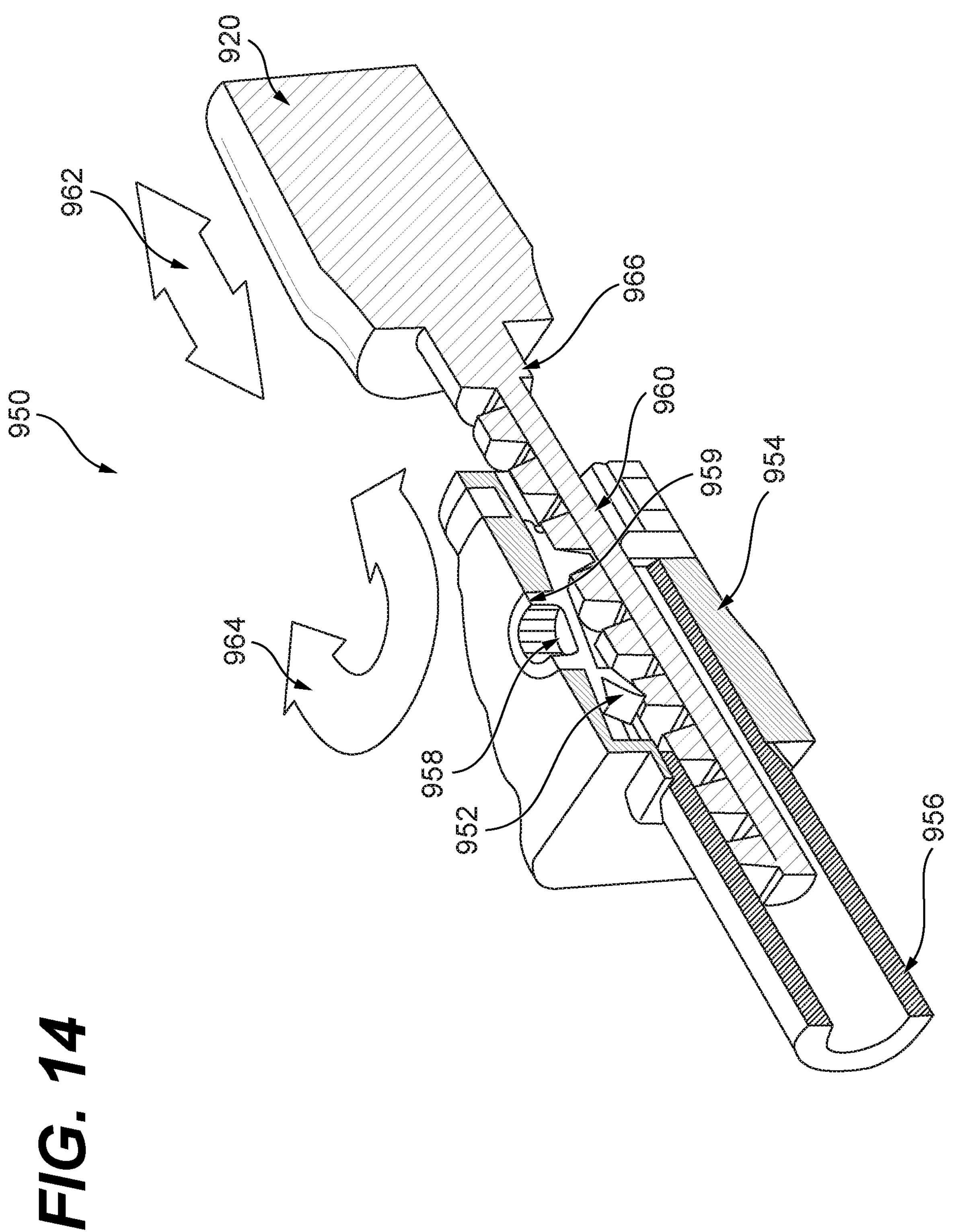
FIG. 14 is a side view of a first embodiment of a neck expansion and contraction mechanism trial femoral neck rotated ninety degrees from FIG. 13 with a cutaway view of a notched rod interacting with the tilted spiral cam with the notched rod extended and attached to the head and the bottom of the notched rod secured in a circular lower neck enclosure.

Referring to FIGS. 12-14, a first embodiment of a neck lengthening device 950 is shown. Positioned below the trunnion 920 is notched rod 960 with surfaces that connect to surfaces of a tilted spiral cam 952. The tilted spiral cam 952 is located within housing 954. This neck lengthening device 950 provides an extension of the neck portion 966, shown in FIG. 14, that cannot be back driven by pressure from the tissue or rotation of the trunnion 920. The amount of extension 966 of the trunnion 920 can be accurately controlled or precisely "dialed in" based on the dimensions of the tilted spiral cam 952. The tilted spiral cam 952 includes a protrusion 958 that engages an opening 959 in the housing 954 to provide a securing mechanism. The longitudinal neck movement is generally indicated by the numeral 962, and the circular spiral cam movement that is converted to longitudinal neck movement is indicated by the numeral 964. Housing 954 is positioned above the neck portion 956, which is cylindrical and encloses the notched rod 960.

Figure 15:
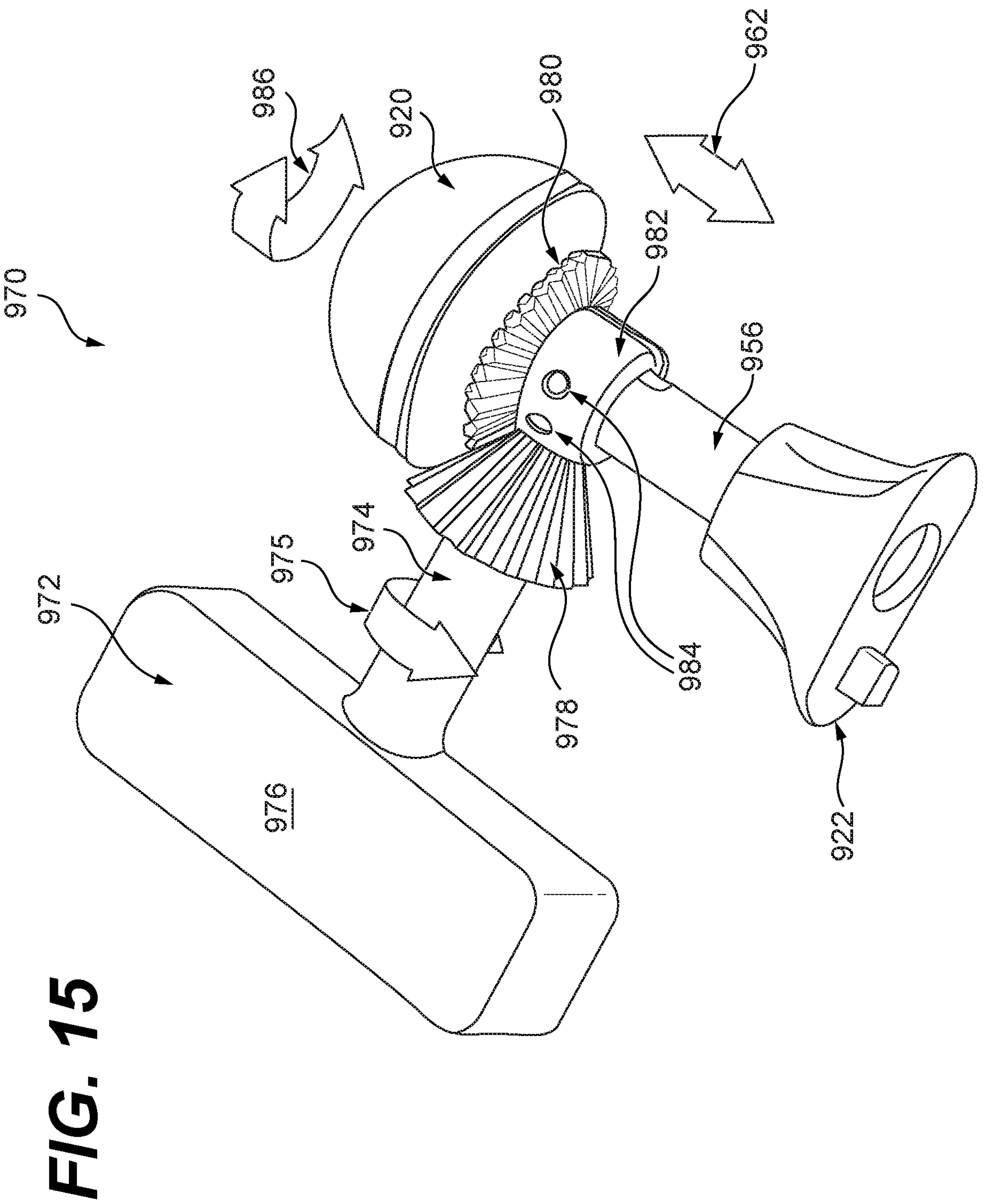
FIG. 15 is a perspective view of a second embodiment for a neck expansion and contraction mechanism trial femoral neck that includes a driver tool that rotates a bevel pinion gear that engages a bevel gear on a head that expands or contracts the length of the neck.
Figure 16:
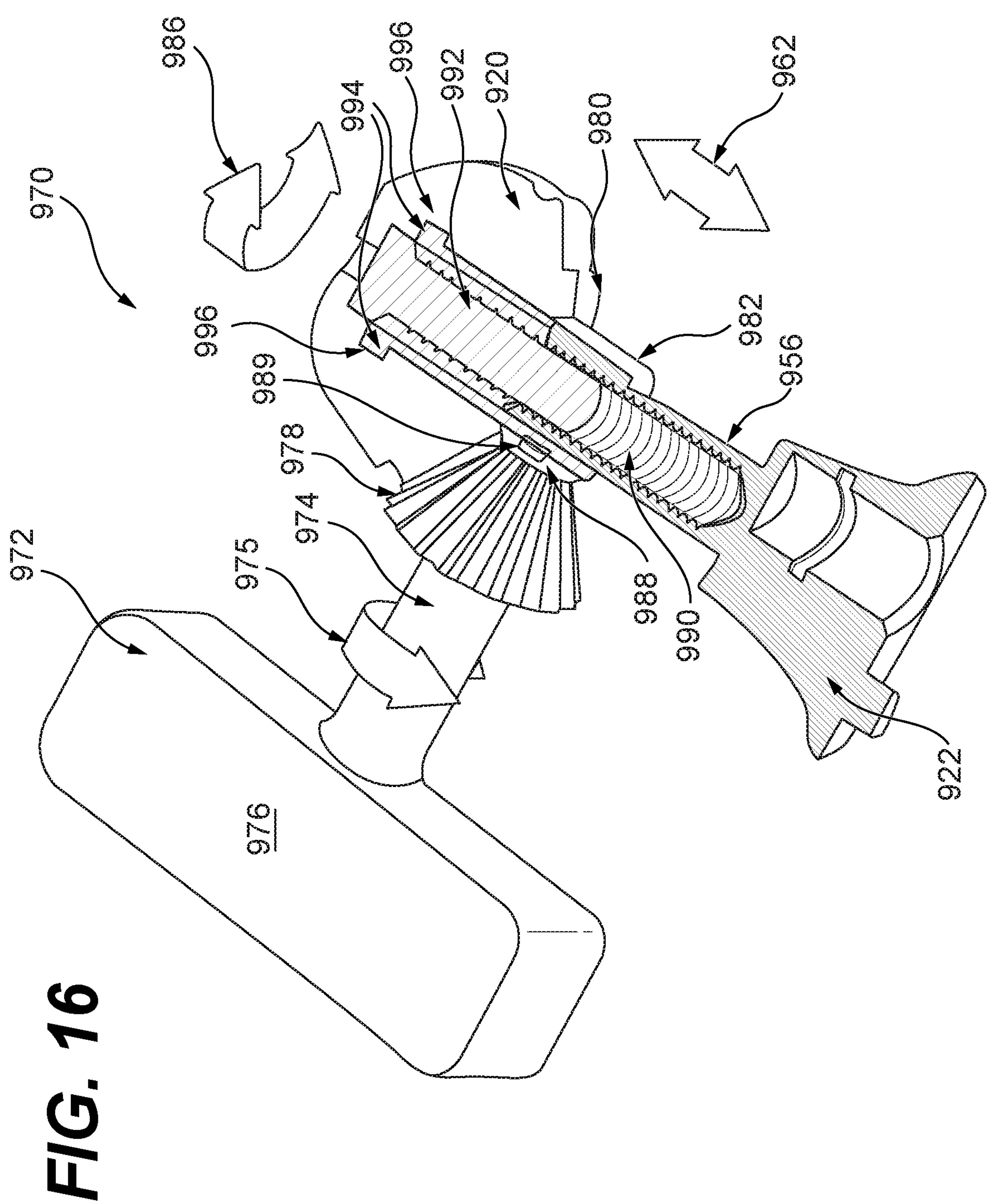
FIG. 16 is a perspective cutaway view of a second embodiment for a neck expansion and contraction mechanism trial femoral neck that includes a driver tool that rotates a bevel pinion gear that engages a bevel gear on a head that expands or contracts a length of a neck by engaging a screw located within a coupling sleeve that is secured within a head.

Turning next to FIGS. 15-16, a second embodiment of a neck lengthening device 970 is shown. There is a driver tool 972 that provides a rotational force. Numerous embodiments of various types of tools can provide this type of rotational force comparable to a hand drill. The driver tool 972 includes an enclosed rotating shaft 974 that is attached to a bevel pinion gear 978. The direction of rotation of the rotating shaft 974 is indicated by the numeral 975. The bevel pinion gear 978 engages a bevel gear 980 that is attached to the trunnion 920 with the rotation indicated by the numeral 986. As before, the neck portion 956 is positioned on top of the stem 922.

As shown in FIG. 15, coupling sleeve 982 is disposed about the neck portion 956 and affixed in position by connecting screws 984. Coupling sleeve 982 serves to couple the bevel pinion gear 978 with the neck portion 956. As shown in FIG. 16, the coupling sleeve 982 includes a bushing 988 that retains a circular protrusion 989 associated with the bevel pinion gear 978. The coupling sleeve 982 may further include a retained flange 994 as an upper component of the coupling sleeve 982. The retained flange 994 may be secured by a slot 996 in the trunnion 920. The bevel gear 980 is adapted to engage a screw 992, rotatable in a threaded internal passage 990 within the neck portion 956, that provides the power to extend and retract the trunnion 920. The bevel gear 980 is also connected to the coupling sleeve 982, which serves to provide proper alignment of the bevel pinion gear 978 and bevel gear 980 for engagement, as well as provide a bearing surface to guide the extension and retraction of neck portion 956 indicated by numeral 962.

Figure 17:
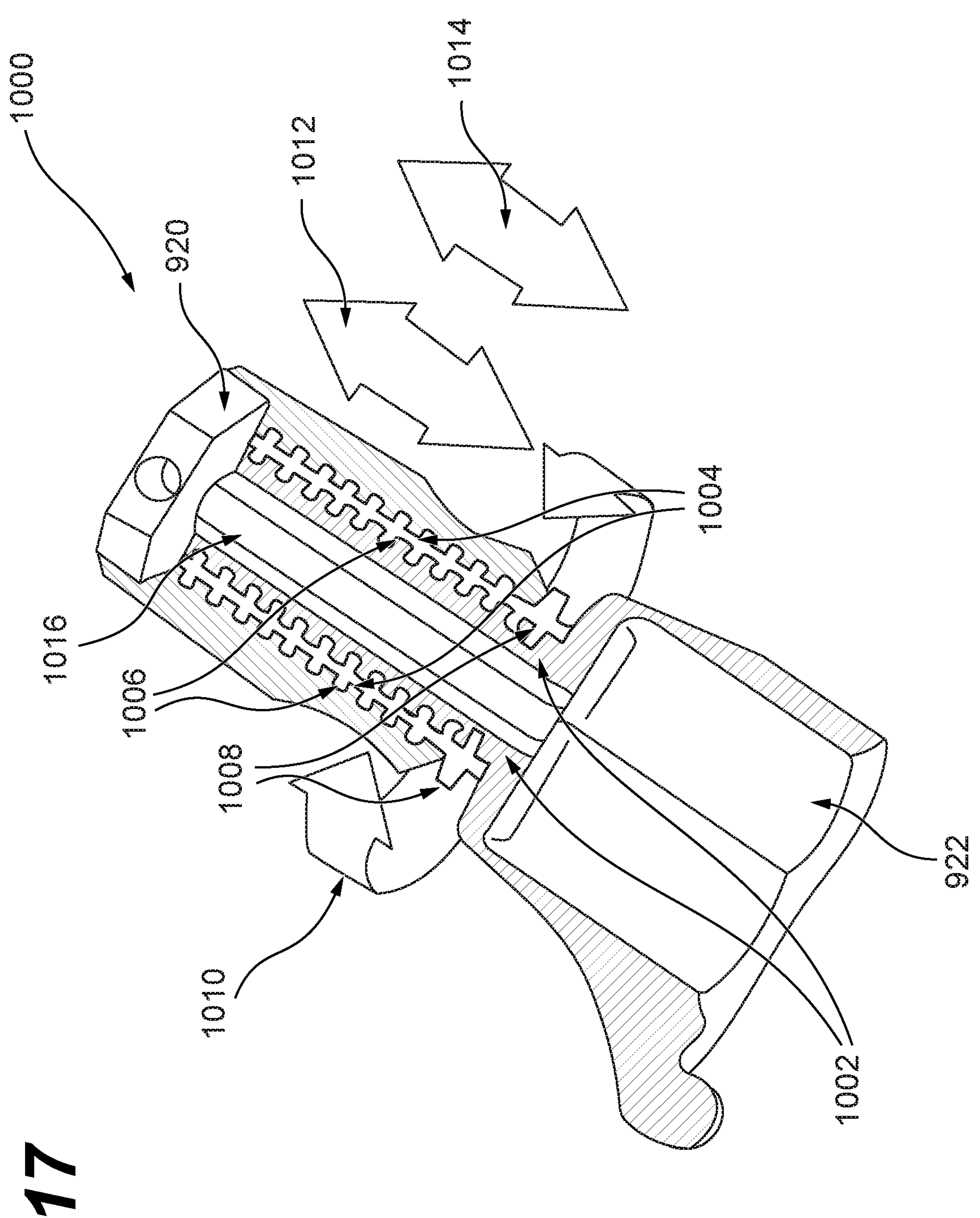
FIG. 17 is a cutaway perspective view of a third embodiment for a neck expansion and contraction mechanism trial femoral neck that includes a first nested, telescoping threaded element attached to the stem, a third nested, telescoping threaded element attached to the head, and a second nested, telescoping threaded element located between the first nested, telescoping threaded element and the third nested, telescoping threaded element with a threaded nut that can travel up and down the second nested, telescoping threaded element and an anti-rotation guide located between the second nested, telescoping threaded element and the third nested, telescoping threaded element to lock rotation of the second nested, telescoping threaded element and the third nested, telescoping threaded element in relationship to each other in a contracted position.
Figure 18:
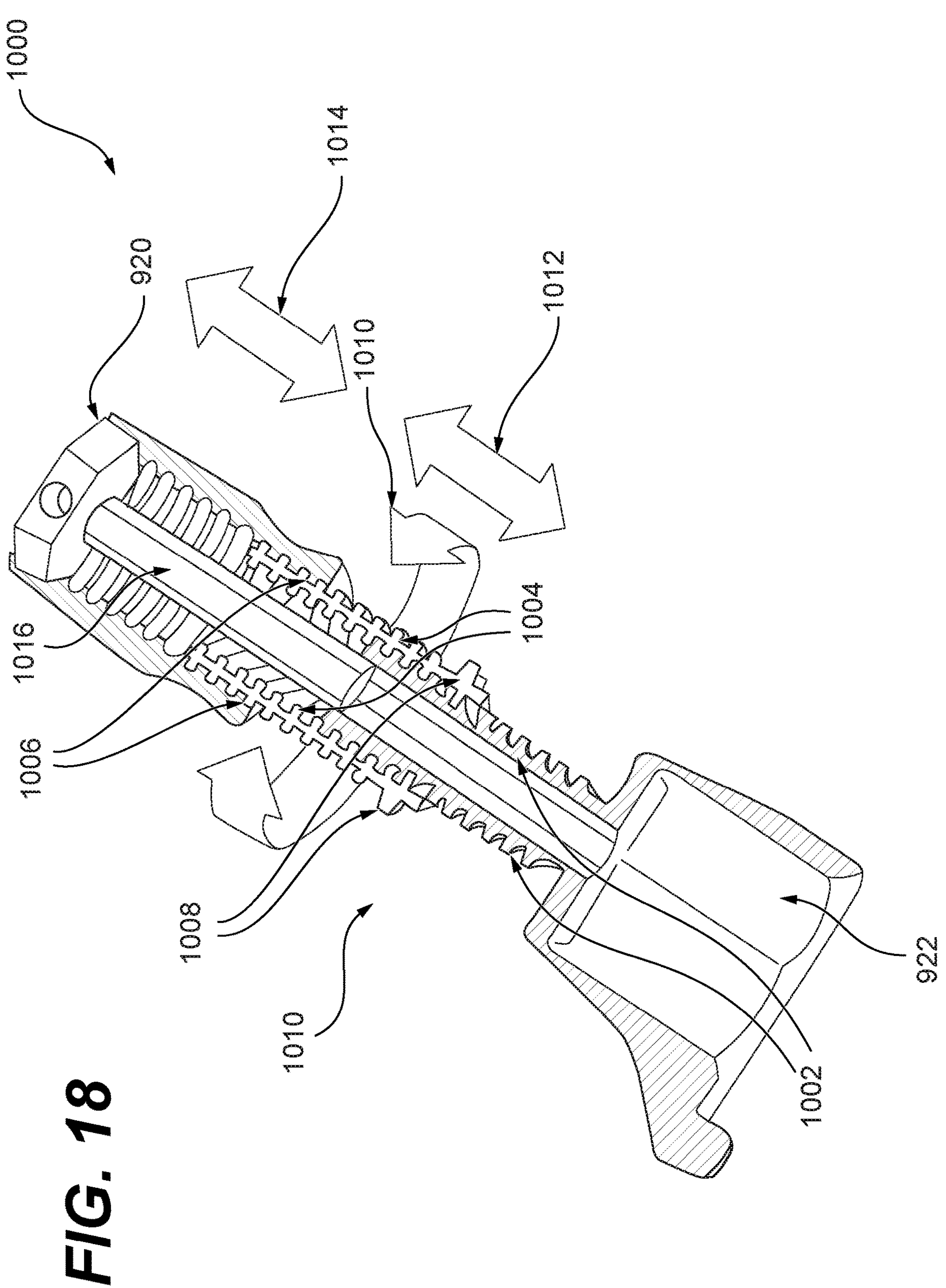
FIG. 18 is a cutaway perspective view of a third embodiment for a neck expansion and contraction mechanism trial femoral neck shown in FIG. 17 that includes a first nested, telescoping threaded element attached to the stem; a third nested, telescoping threaded element attached to the head, and a second nested, telescoping threaded element located between the first nested, telescoping threaded element and the third nested, telescoping threaded element with a threaded nut that can travel up and down the second nested, telescoping threaded element and an anti-rotation guide located between the second nested, telescoping threaded element and the third nested, telescoping threaded element to lock rotation of the second nested, telescoping threaded element and the third nested, telescoping threaded element in relationship to each other in an expanded position.
Figure 19:
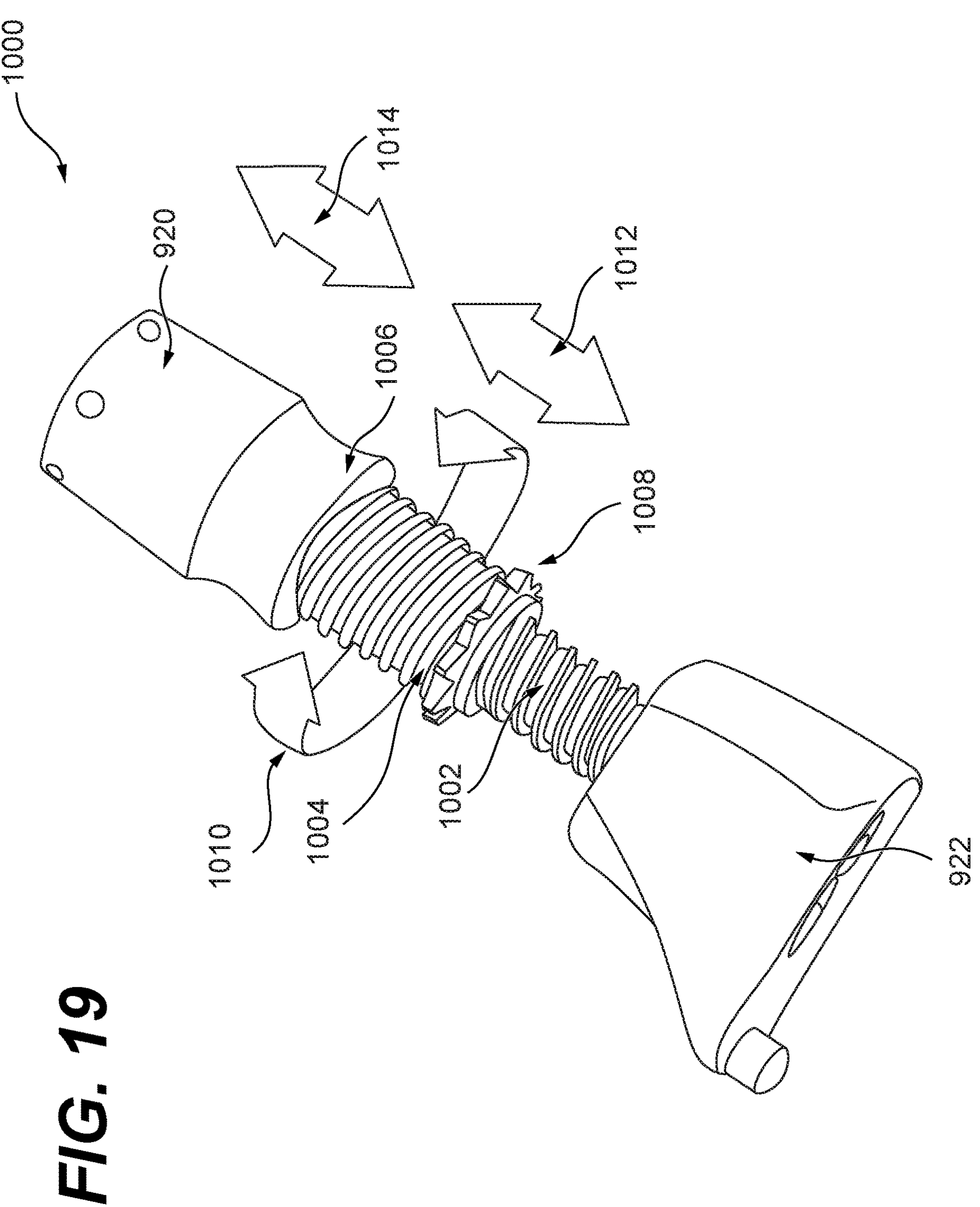
FIG. 19 is a perspective view of a third embodiment for a neck expansion and contraction mechanism trial femoral neck shown in FIG. 17 that includes a first nested, telescoping threaded element attached to the stem; a third nested, telescoping threaded element attached to the head, and a second nested, telescoping threaded element located between the first nested, telescoping threaded element and the third nested, telescoping threaded element with a threaded nut that can travel up and down the second nested, telescoping threaded element and an anti-rotation guide located between the second nested, telescoping threaded element and the third nested, telescoping threaded element to lock rotation of the second nested, telescoping threaded element and the third nested, telescoping threaded element in relationship to each other in an expanded position.

A third embodiment of a neck lengthening device is generally indicated by the numeral 1000 in FIGS. 17, 18, and 19. This neck lengthening device 1000 includes nested, telescoping, threaded elements, e.g., three such elements, with oppositely handed threads. In an illustrative, but non-limiting, embodiment, a first nested, telescoping threaded element 1002, e.g., right-hand screw, has an external thread running in one direction, e.g., clockwise, with a nut 1008 with matching internal thread that can go up and down the first nested, telescoping threaded element 1002.

This nut 1008 also has an external thread of opposite handedness, e.g., counterclockwise, which engages a third nested, telescoping threaded element 1006, preferably with a matching internal thread, e.g., counterclockwise. This third nested, telescoping threaded element 1006 is connected to the first nested, telescoping threaded element 1002 via an anti-rotation guide 1016, which locks the rotation of the first nested, telescoping threaded element 1002 and third nested, telescoping threaded element 1006. When the second nested, telescoping, threaded element 1004 is rotated, it rides up the first nested, telescoping threaded element 1002 and forces the third nested, telescoping threaded element 1006 to extend in the same direction. Because all threaded elements 1002, 1004, and 1006 are nested inside each other and are "telescoping," they maintain overlap from 50% to 100% at any one time, providing bending rigidity for this extending structure. Rotational movement is generally indicated by the numeral 1010 of the threaded elements 1002, 1004, and 1006.

Also, because the third nested, telescoping threaded element 1006 is not rotating relative to the first nested, telescoping threaded element 1002 that forms a base element, the rotation of the trunnion trial 920 does not affect the overall length of the neck lengthening device 1000. The longitudinal extension and contraction of the second nested, telescoping, threaded element 1004 is indicated by numeral 1012, and the longitudinal extension and contraction of the third nested, telescoping, threaded element 1006 is indicated by numeral 1014.

Leg Length and Offset Tracking

In use, the adjustment of trial femoral head and neck assembly 910 as described herein causes associated changes in leg length and offset measurements of the patient. These dimensions may be monitored and assessed during trialing workflows in order to determine the ideal configuration for a patient's anatomy. For example, when a desired leg length and offset are achieved, the position, e.g., the extent of expansion of the trial femoral head and neck assembly 910 may reflect the correct size and configuration for a femoral head and neck assembly implant. FIGS. 20-26 illustrate methods and devices which may be used to track leg length and offset in a patient during a THA procedure, and more particularly, during trialing of femoral head and neck implants.

Figure 20:
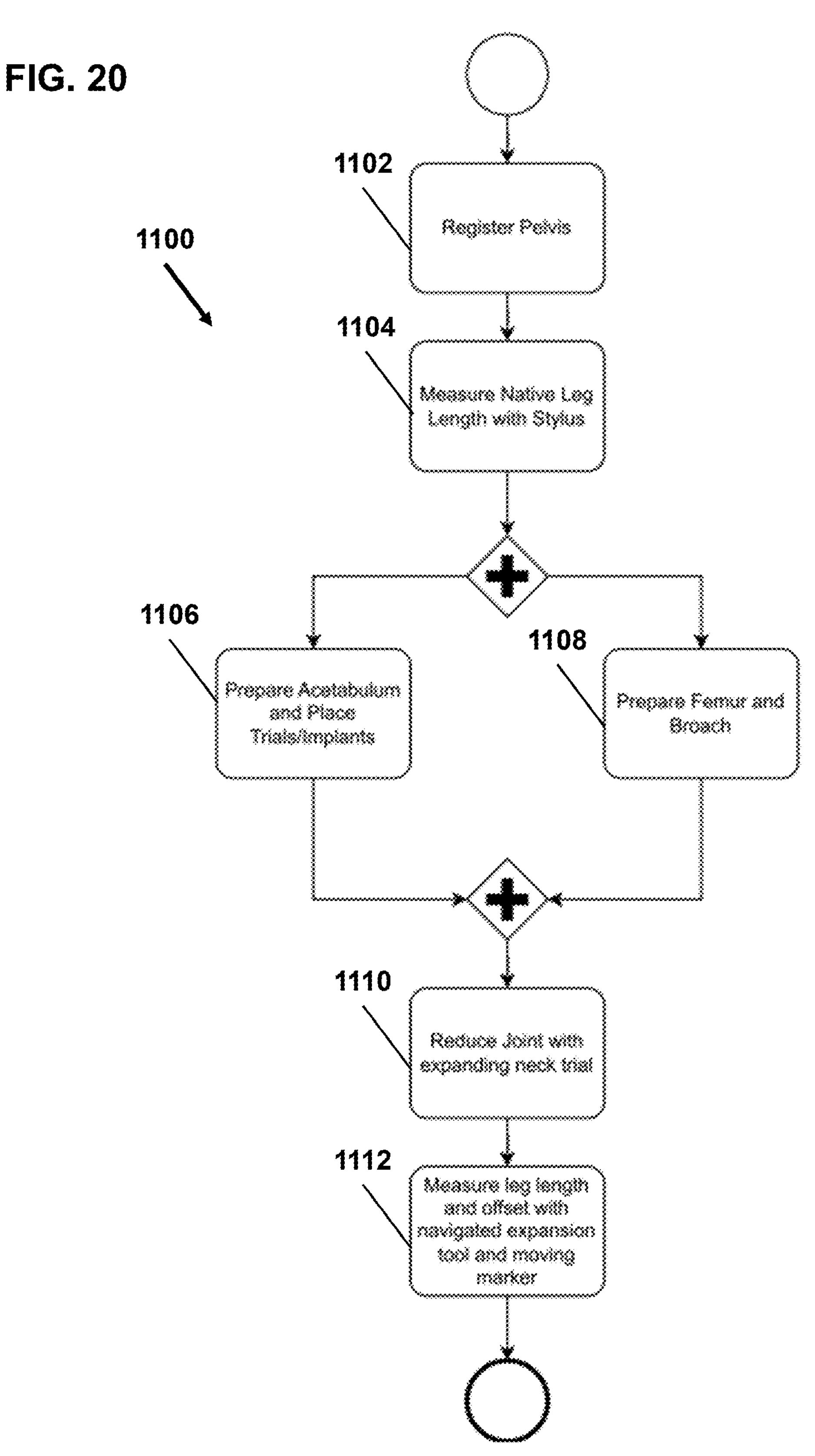
FIG. 20 shows a process flow diagram for measuring leg length and offset, according to an embodiment of the disclosure.
Figure 21:
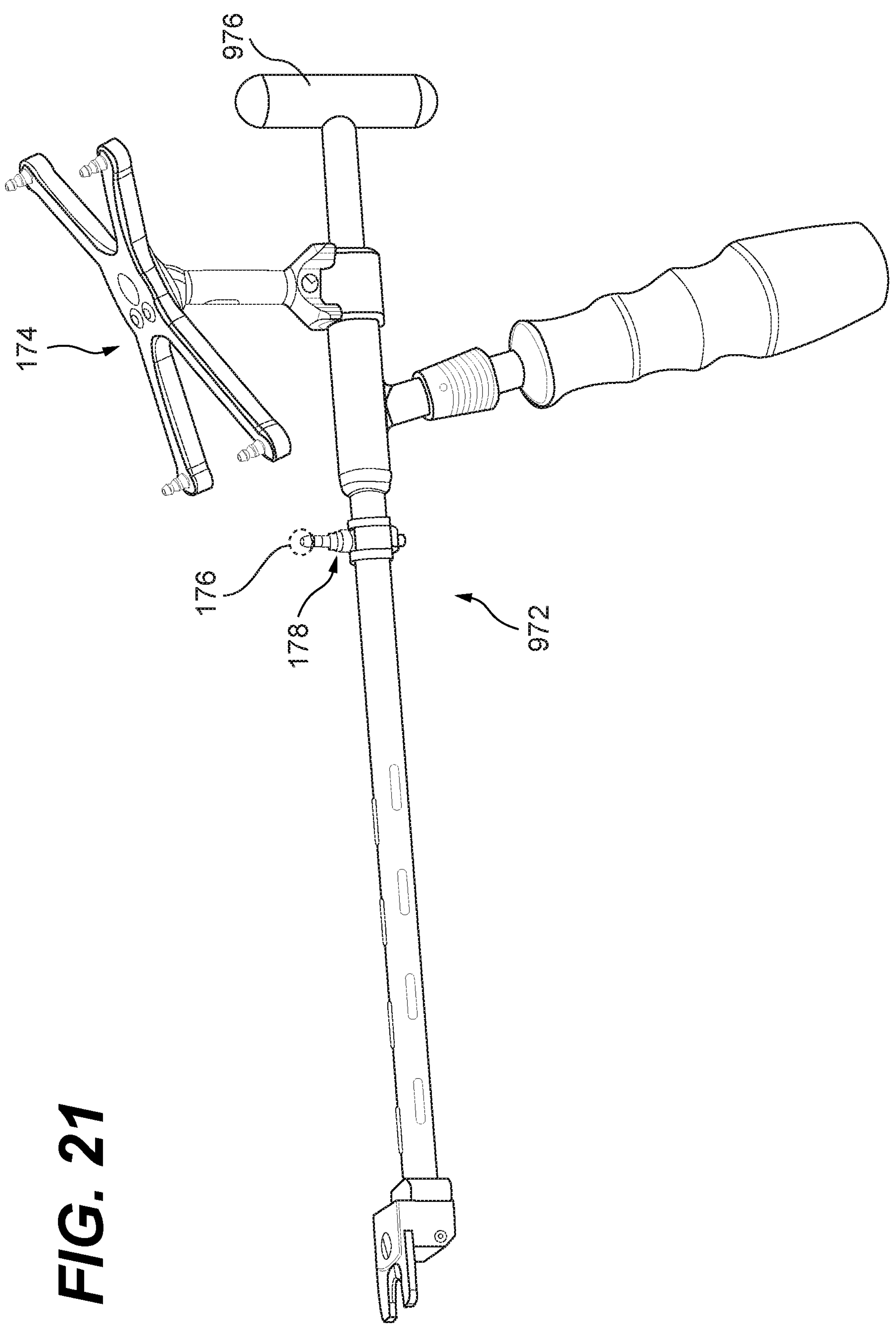
FIG. 21 shows a perspective view of an expandable driver with accessories for actively tracking leg length, in accordance with embodiments of the disclosure.
Figure 22:
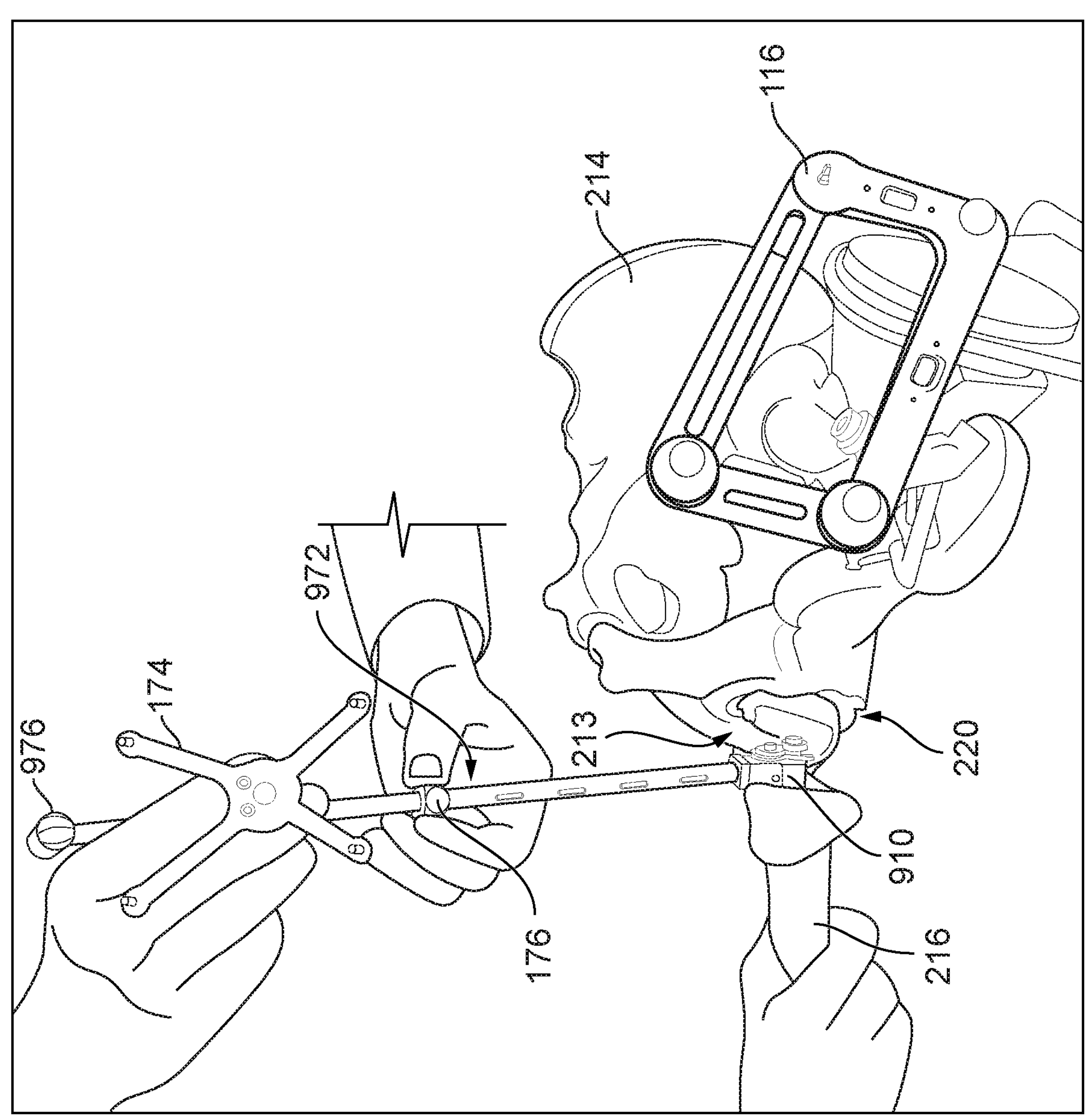
FIG. 22 shows a portion of the process of tracking leg expansion with a tracking array on an expandable driver, in accordance with embodiments of the disclosure.

Turning first to FIGS. 20-22, a first workflow 1100 is provided in FIG. 20, and portions thereof are illustrated in FIGS. 21-22, for tracking leg length and/or offset during the use of an expandable trial femoral assembly 910 as described herein.

A first process 1102 in workflow 1100 includes registering the patient's pelvis 214 to a navigated surgical system (or, "computer-assisted surgical navigation system") such as, e.g., surgical system 10 as described above and depicted in FIGS. 1-6. In certain embodiments, the process 1102 of registering the patient's pelvis 214 may include rigidly affixing a dynamic reference base (DRB) 116 to the pelvis 214. The DRB 116 may be used in combination with the camera tracking system 200 (FIGS. 1-4) to register the pelvis 214 to the surgical system 10 as previously described.

Figure 24:
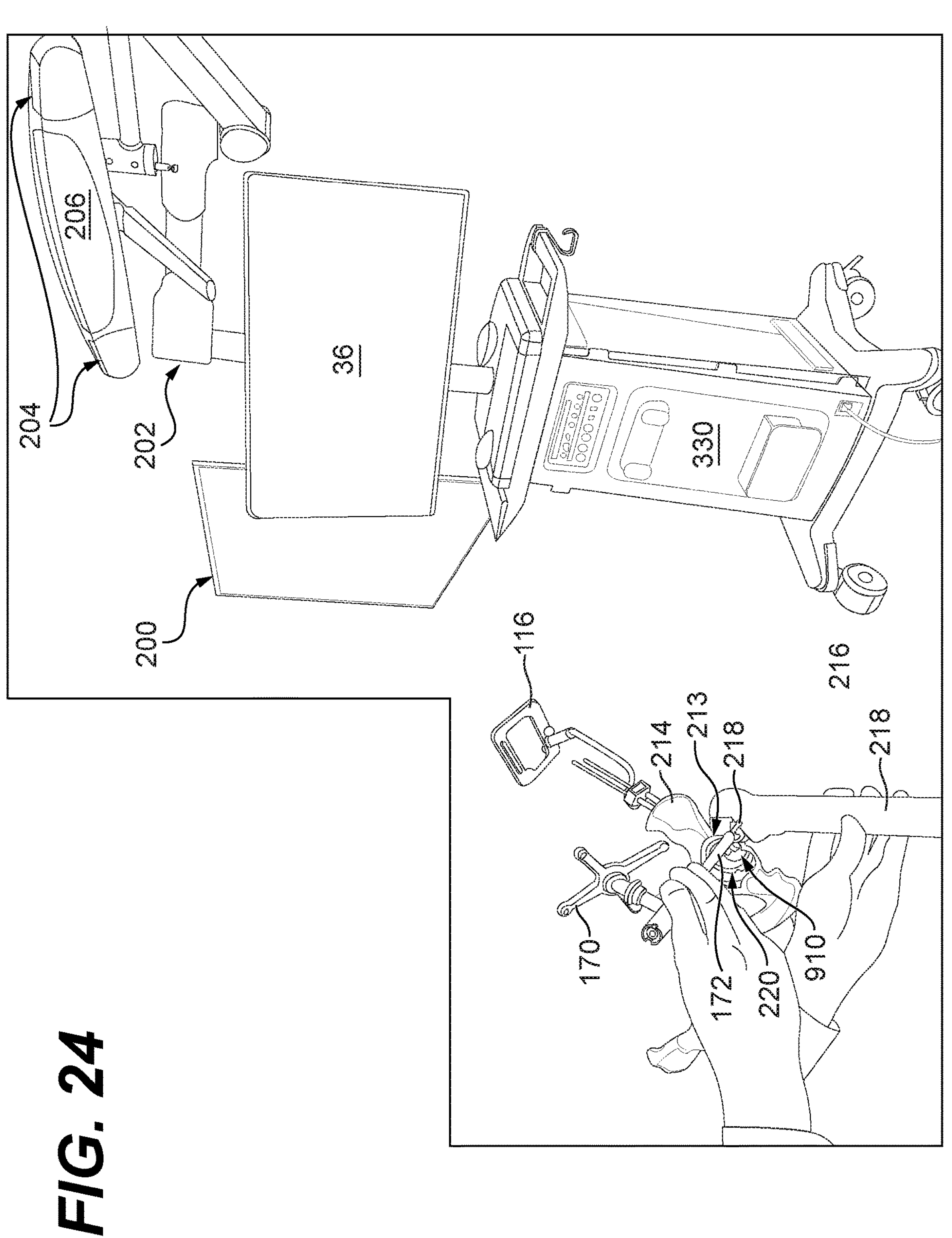
FIG. 24 shows a portion of the process of intermittently placing a stylus on the created checkpoint on the femur to capture leg length change, in accordance with embodiments of the disclosure.

A second process 1104 includes acquiring a measurement, e.g., measuring a native leg length of the patient using a navigated instrument. In certain embodiments, the navigated instrument may be a stylus 172, which may further include an instrument reference element 170 in the form of a tracking array disposed thereon, as seen in FIG. 24. The instrument reference element 170 may include a plurality of tracking markers such as, e.g., NIR retroreflective, NIR LED, visible, etc. markers, which are capable of being tracked by the camera tracking system 200 and are calibrated to the image space of 2D and/or 3D images as previously described. In order to measure a native leg length of the patient, the stylus 172 may be used to palpate the patient's leg, e.g., femur, or paint a surface of the patient's leg. The acquired data (single point or surface painting) may be used by the surgical system 10 to determine the native leg length of the patient. This native leg length may be displayed to the surgeon, e.g., on display 36 or XR headset 150.

After the native leg length is acquired, process 1106 is performed, including preparing the patient's acetabulum 213 to receive an acetabular prosthesis 220. This may include, e.g., reaming the acetabulum 213. Following preparation of the acetabular surface, a suitable trial or implant 220 may be placed, such as, e.g., an acetabular prosthesis or "shell," which may include a trial shell.

Either before, during, or after the performance of process 1106, process 1108 may be performed, in which the patient's femur 216 is prepared. Preparation of the femur 216 may include, e.g., reaming and broaching the femoral canal, to form a broach suitable to receive a femoral head and neck assembly therein.

Process 1110 includes affixing an expandable trial femoral assembly 910 to the femur 216 of the patient, which was previously prepared according to process 1108. As discussed previously, the expandable femoral assembly 910 includes an adjustable femoral neck portion 912 (FIGS. 10-11) adapted to couple with a femoral head implant. The adjustable femoral neck portion 912 is adapted to be received within the broach. The joint, including the expandable trial femoral assembly 910 and the trial shell, is then reduced.

Process 1112 includes adjusting an expansion extent of the expandable trial femoral assembly 910, e.g., expanding or collapsing the adjustable neck portion 912 thereof, and measuring a resulting leg length of the patient. As shown in FIGS. 21-22, a driver 972 is provided, having a first reference element 174 disposed thereon. The first reference element 174 may be a tracking array that is analogous in structure and function to instrument reference element 170 disposed on the stylus 172, but is distinct therefrom in that the first reference element 174 identifies and permits tracking of a distinct navigated instrument, e.g., driver 972, by the camera tracking system 200. Collectively, the driver 972 and the first reference element 174 may be referred to as a navigated driver. The navigated driver may include a knob 976 which may be actuated, e.g., rotated in order to adjust an expansion extent of the expandable trial femoral assembly when the distal tip of the driver 972 is engaged with the expandable trial femoral assembly 910 as described herein above. The adjusting may include, e.g., expanding or collapsing the expandable trial femoral assembly 910 as described relative to FIG. 10.

Referring back to FIGS. 21-22, the driver 972 may further include a second reference element 176. The second reference element 176 may be a single tracking marker, and may be disposed, coupled, or otherwise affixed to a movable mount, e.g., a movable length indicator post 178 on the driver 972. As the knob 976 is actuated, e.g., rotated, to adjust the expansion extent of the expandable neck 912 of the assembly 910, the post 178 carrying second reference element 176 is configured to move, e.g. translate proximally or distally, relative to the first reference element 174. In this manner, the second reference element 176 serves as a leg length indicator. The distance moved by the second reference element 176 relative to the first reference element 174 is perceptible to the camera tracking system 200, and may be used by the surgical system 10 to determine a measurement, i.e. to measure one or both of the leg length or the offset of the patient. In this manner, the distance moved by the second reference element 176 relative to the first reference element 174 is representative of one or both of the leg length or the offset of the patient.

This process may be performed iteratively. For example, the surgeon may adjust the assembly 910 and determine the leg length and/or offset that results from the adjustment via the detected position of the second reference element 176, and may repeat that process iteratively until a desired leg length and offset are achieved. Each adjustment may be independently selected from expansion and collapse of the assembly 910, depending on the desired adjustment. At each determination, the leg length and/or offset may then be displayed to the surgeon, e.g., via a display, which may include an XR headset 150 as described herein above.

Figure 23:
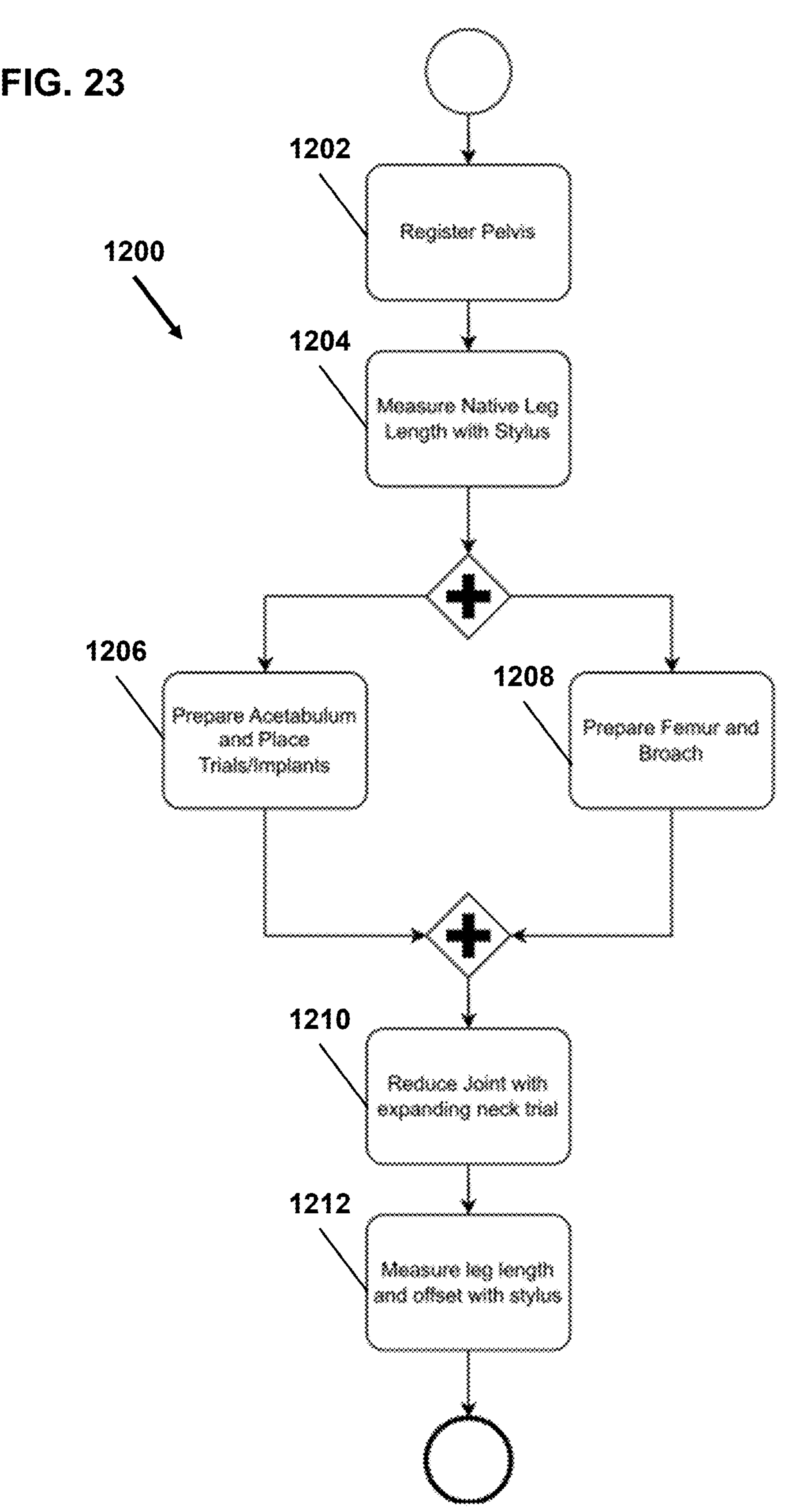
FIG. 23 shows a process flow diagram for measuring leg length and offset, according to an embodiment of the disclosure.

Turning next to FIGS. 23-24, a second workflow 1200 is provided in FIG. 23, and portions thereof are illustrated in FIG. 24, for tracking leg length and/or offset during the use of an expandable trial femoral assembly 910 as described herein. A first process 1202 includes registering the pelvis 214 of the patient to a navigated surgical system (or, "computer assisted navigated surgical system") such as, e.g., surgical system 10 as described above and depicted in FIGS. 1-6. In certain embodiments, the process 1202 of registering the patient's pelvis 214 may include rigidly affixing a DRB 116 to the pelvis 214 of the patient. The DRB 116 may be used in combination with the camera tracking system 200 (FIGS. 1-4) to register the pelvis 214 to the surgical system 10 as previously described.

A second process 1204 includes acquiring a measurement, e.g., measuring a native leg length of the patient using a navigated instrument. In certain embodiments, the navigated instrument may be a stylus 172, which may further include an instrument reference element 170 in the form of a tracking array disposed thereon, as seen in FIG. 24. Collectively, the stylus 172 and the reference element 170 may be referred to as a navigated instrument or a navigated stylus. The instrument reference element 170 may include a plurality of tracking markers such as, e.g., NIR retroreflective, NIR LED, visible, etc. markers, which are capable of being tracked by the camera tracking system 200 and are calibrated to the image space of 2D and/or 3D images as previously described. In order to measure a native leg length of the patient, a checkpoint punch may be used to create one or more checkpoints 218 on the femur 216 of the patient, and the checkpoint may be contacted or palpated one or more times by the stylus 172. The point data acquired by the navigated stylus 172 may be used by the surgical system 10 to determine the native leg length of the patient.

After the native leg length is acquired, process 1206 is performed, including preparing the patient's acetabulum 213 to receive an acetabular prosthesis 220. This may include, e.g., reaming the acetabulum 213. Following preparation of the acetabular surface, a suitable trial or implant 220 may be placed, such as, e.g., an acetabular prosthesis or "shell," which may include a trial shell.

Either before, during, or after the performance of process 1206, process 1208 may be performed, in which the patient's femur 216 is prepared. Preparation of the femur 216 may include, e.g., reaming and broaching the femoral canal such that the prepared femoral canal is adapted to receive a femoral head and neck assembly within the broach.

Process 1210 includes affixing an expandable trial femoral assembly 910 to the femur 216 of the patient, which was previously prepared according to process 1208. As discussed previously, the expandable femoral assembly 910 includes an adjustable femoral neck portion 912 (FIGS. 10-11) adapted to couple with a femoral head implant. The adjustable femoral neck portion 912 is adapted to be received within the broach. The joint, including the expandable trial femoral assembly 910 and the trial shell, is then reduced.

Process 1212 includes adjusting an expansion extent of the expandable trial femoral assembly 910, e.g., expanding or collapsing the adjustable neck portion 912 thereof, and measuring a resulting leg length of the patient. Adjusting the expansion extent of the expandable trial femoral assembly 910, i.e. expanding or collapsing the assembly 910, may be performed using a driver 972 (FIGS. 15-16), e.g., by actuating a knob of the driver when the distal tip of the driver 972 is engaged with the expandable trial femoral assembly 910 as described herein above. As the assembly 910 is adjusted, i.e. expanded or collapsed, the leg length of the patient may be measured by contacting the stylus 172 to the checkpoint 218 on the femur 216 to capture a position of the checkpoint 218. This change in position may be captured by the camera tracking system 200, relative to the tracking coordinate system. This position may then be used by the surgical system 10 to determine a measurement of the leg length or the offset that exists when the checkpoint 218 is in the position at which the data point was acquired, e.g., when the assembly 910 is adjusted to the expansion extent at which the data point was acquired. In various embodiments, the stylus may be used to contact or palpate the checkpoint 218 a plurality of times, which may occur intermittently during the adjusting. For example, the surgeon may adjust the assembly 910 and contact the stylus to the checkpoint 218 to determine the leg length and/or offset that results from the adjustment, and may repeat that process iteratively until a desired leg length and offset are achieved. Each adjustment may be independently selected from expansion and collapse of the assembly 910, depending on the desired adjustment. At each determination, the leg length and/or offset may then be displayed to the surgeon, e.g., via a display, which may include an XR headset 150 as described herein above.

Figure 26:
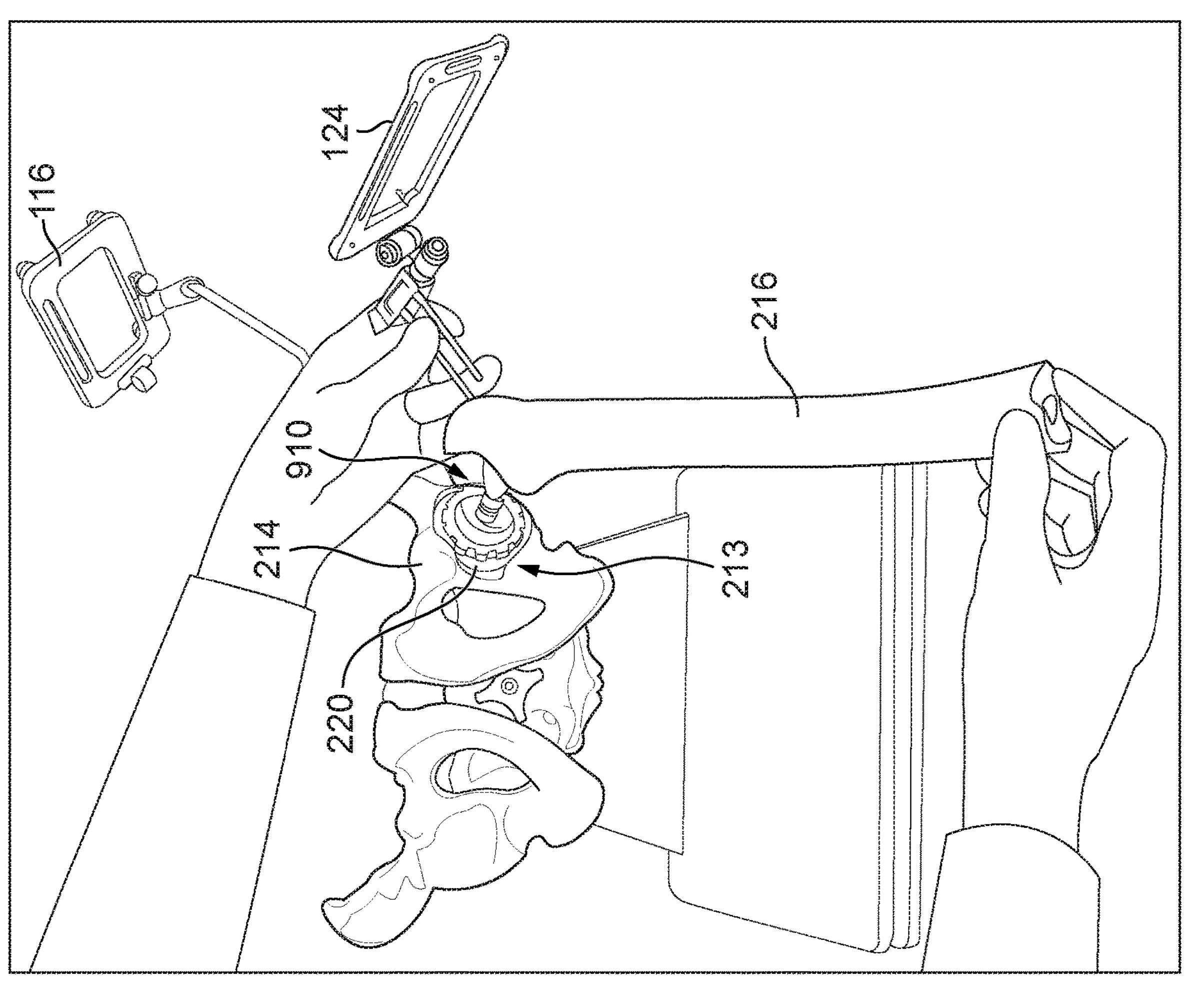
FIG. 26 shows a portion of the process of placing an array on the femur to track position relative to a DRB affixed to the patient's pelvis, in accordance with embodiments of the disclosure.

Turning next to FIGS. 25-26, a third workflow 1300 is provided in FIG. 25, and portions thereof are illustrated in FIG. 26, for tracking leg length and/or offset during the use of an expandable trial femoral assembly 910 as described herein.

A first process 1302 in the workflow 1300 includes registering the patient's pelvis 214 and femur 216 to a navigated surgical system (or, "computer assisted surgical navigation system") such as, e.g., surgical system 10 as described above and depicted in FIGS. 1-6. In certain embodiments, the process 1302 of registering the patient's pelvis 214 may include rigidly affixing a first reference element to the pelvis 214 of the patient. The first reference element may be in the form of, e.g., a DRB 116, described previously herein. Similarly, registering the patient's femur 216 may include rigidly affixing a second reference element to the femur 216 of the patient, which may be in the form of a second DRB 124. The second DRB 124 may be a tracking array that is analogous in structure and function to the first DRB 116, but is distinct therefrom in that the second DRB 124 uniquely identifies and permits tracking of a distinct anatomical feature, e.g., the femur 216, by the camera tracking system 200. The DRBs 116, 124 may be used in combination with the camera tracking system 200 (FIGS. 1-4) to register the pelvis 214 and femur 216, respectively, to the surgical system 10 as previously described.

A second process 1304 includes preparing the patient's acetabulum 213 to receive an acetabular prosthesis 220. This may include, e.g., reaming the acetabulum 213. Following preparation of the acetabular surface, a suitable trial or implant 220 may be placed, such as, e.g., an acetabular prosthesis or "shell," which may include a trial shell.

Either before, during, or after the performance of process 1304, process 1306 may be performed, in which the patient's femur 216 is prepared. Preparation of the femur 216 may include, e.g., reaming and broaching the femoral canal such that the prepared femoral canal is adapted to receive a femoral head and neck assembly within the broach.

Process 1308 includes affixing an expandable trial femoral assembly 910 to the femur 216 of the patient, which was previously prepared according to process 1306. As discussed previously, the expandable femoral assembly 910 includes an adjustable femoral neck portion 912 (FIGS. 10-11) adapted to couple with a femoral head implant. The adjustable femoral neck portion 912 is adapted to be received within the broach. The joint, including the expandable trial femoral assembly 910 and the trial shell, is then reduced.

Once the joint is reduced, the expansion extent of the expandable trial femoral assembly 910 may be adjusted, i.e. expanded or collapsed, using a driver 972 (FIGS. 15-16), e.g., by actuating a knob 976 of the driver 972. As the expandable trial femoral assembly 910 is adjusted, the patient's associated leg length and offset will change. This change may be tracked using the navigated surgical system. In particular, the second DRB 124, affixed to the femur 216, will move relative to the first DRB 116, affixed to the pelvis, as the trial femoral assembly 910 is expanded or collapsed by actuating the driver 972, e.g., knob 976, in one rotational direction or the other. The movement of the second DRB 124 relative to the first DRB 116 may be tracked and captured by the camera tracking system 200, and used to determine and track the associated leg length and/or offset of the patient, which may be at least in part a function of the expansion extent of the expandable trial femoral assembly 910.

For example, the surgeon may adjust the assembly 910 and determine the leg length and/or offset that results from the adjustment based on the movement of DRB 124 relative to DRB 116. The surgeon may then repeat that process iteratively until a desired leg length and offset are achieved. Each adjustment may be independently selected from expansion and collapse of the assembly 910, depending on the desired adjustment. At each determination, the leg length and/or offset may then be displayed to the surgeon, e.g., via a display, which may include an XR headset 150 as described herein above.

Further Definitions and Embodiments

In the above description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected," "coupled," "responsive," or variants thereof to another element, it can be directly connected, coupled, or responsive to the other element or intervening elements may be present. In contrast, when an element is referred to as being "directly connected," "directly coupled," "directly responsive," or variants thereof to another element, there are no intervening elements present. Like numbers refer to like elements throughout. Furthermore, "coupled," "connected," "responsive," or variants thereof as used herein may include wirelessly coupled, connected, or responsive. As used herein, the singular forms "a," "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise," "comprising," "comprises," "include," "including," "includes," "have," "has," "having," or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.," which derives from the Latin phrase "exempli gratia," may be used to introduce or specify a general example or examples of a previously mentioned item, and is not intended to be limiting of such item. The common abbreviation "i.e.," which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A method of tracking one or both of a leg length or an offset in a patient during a total hip arthroplasty (THA) procedure, the method comprising:

registering a pelvis of the patient to a navigated surgical system;

measuring a native leg length of the patient using a navigated instrument;

affixing an expandable trial femoral assembly to a prepared and broached femur of the patient;

reducing the expandable trial femoral assembly into an acetabular prosthesis; and using a navigated driver having a first reference element and a second reference element movable relative to the first reference element, adjusting an expansion extent of the expandable trial femoral assembly; and measuring one or both of the leg length or the offset in the patient based on a position of the first reference element relative to the second reference element as detected by the navigated surgical system.

2. The method of claim 1, wherein a distance moved by the second reference element relative to the first reference element is representative of one or both of the leg length or the offset of the patient.

3. The method of claim 1, wherein the first reference element is a tracking array affixed to the navigated driver, and the second reference element comprises a length indicator disposed on a movable mount.

4. The method of claim 1, wherein adjusting the expansion extent of the expandable trial femoral assembly further comprises:

actuating a knob of the navigated driver to expand or collapse the expandable trial femoral assembly.

5. The method of claim 1, further comprising:

affixing a dynamic reference base (DRB) to the pelvis of the patient; and using the DRB to register the pelvis to the navigated surgical system.

6. The method of claim 1, wherein the navigated instrument comprises a stylus having a tracking array disposed thereon.

7. The method of claim 1, wherein the expandable trial femoral assembly comprises a head;

a neck connected to the head; and a stem or broach connected to the neck, wherein the neck is expandable and collapsible.

* * * * *